(12) United States Patent
Uhl et al.

(10) Patent No.: US 12,390,535 B2
(45) Date of Patent: Aug. 19, 2025

(54) METHOD OF MAKING ORAL DOSAGE FORMS

(71) Applicant: UNIVERSITÄT HEIDELBERG, Heidelberg (DE)

(72) Inventors: Philipp Uhl, Heidelberg (DE); Max Sauter, Heidelberg (DE); Walter-Emil Haefeli, Neckargemünd (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 1199 days.

(21) Appl. No.: 17/274,555

(22) PCT Filed: Sep. 27, 2019

(86) PCT No.: PCT/EP2019/076285
§ 371 (c)(1),
(2) Date: Mar. 9, 2021

(87) PCT Pub. No.: WO2020/065054
PCT Pub. Date: Apr. 2, 2020

(65) Prior Publication Data
US 2022/0001021 A1    Jan. 6, 2022

(30) Foreign Application Priority Data

Sep. 28, 2018  (EP) .................... 18197651

(51) Int. Cl.
*A61K 47/64* (2017.01)
*A61K 9/00* (2006.01)
*A61K 47/69* (2017.01)

(52) U.S. Cl.
CPC .......... *A61K 47/645* (2017.08); *A61K 9/0053* (2013.01); *A61K 47/6911* (2017.08)

(58) Field of Classification Search
CPC . A61K 47/645; A61K 47/6911; A61K 9/0053
See application file for complete search history.

(56) References Cited

U.S. PATENT DOCUMENTS

| | | | |
|---|---|---|---|
| 6,120,798 A | 9/2000 | Allen et al. | |
| 6,403,117 B1 | 6/2002 | Sprott et al. | |
| 2007/0059353 A1 | 3/2007 | Harashima et al. | |
| 2012/0134931 A1* | 5/2012 | Tsien ................ | A61K 49/0032 424/9.34 |
| 2013/0149374 A1 | 6/2013 | Lee et al. | |
| 2013/0251783 A1 | 9/2013 | Parmentier et al. | |
| 2014/0112979 A1 | 4/2014 | Andreasen et al. | |
| 2014/0243395 A1* | 8/2014 | Rudolph ................ | A61K 47/34 514/772.3 |
| 2014/0335164 A1 | 11/2014 | Cavaco Paulo et al. | |
| 2015/0216800 A1 | 8/2015 | Huang et al. | |
| 2016/0106864 A1 | 4/2016 | Lim et al. | |
| 2017/0281723 A1* | 10/2017 | Pei .......................... | A61P 11/00 |
| 2018/0303956 A1 | 10/2018 | Uhl et al. | |

FOREIGN PATENT DOCUMENTS

| | | | |
|---|---|---|---|
| CN | 1483399 | 3/2004 | |
| CN | 101744768 | 6/2010 | |
| CN | 101966161 | 2/2011 | |
| CN | 103417480 | 12/2013 | |
| CN | 108135846 | 6/2018 | |
| EP | 0 855 179 | 7/1998 | |
| EP | 3158992 A1 * | 4/2017 | ............. A61K 38/08 |
| JP | 10-203964 | 8/1998 | |
| JP | 2016-79182 | 5/2016 | |
| RU | 2 556 800 | 7/2014 | |
| WO | 2010/054326 | 5/2010 | |
| WO | 2011/157713 | 12/2011 | |
| WO | 2013/059617 | 4/2013 | |
| WO | WO-2013059617 A1 * | 4/2013 | ............. A61K 38/08 |
| WO | 2017/067642 | 4/2017 | |

OTHER PUBLICATIONS

International Search Report and Written Opinion of the International Searching Authority, issued Dec. 20, 2019 in corresponding International Patent Application No. PCT/EP2019/076285.
Sharma et al., "Grafting of Cell-Penetrating Peptide to Receptor-Targeted Liposomes Improves their Transfection Efficiency and Transport across Blood-Brain Barrier Model", J. Pharmaceutical Sci., 101(7): 2468-2478 (2012).
Parmentier et al., "Oral peptide delivery by tetraether lipid liposomes", International Journal of Pharmaceutics, 415: 150-157 (2011).
Bashyal et al., "Cell penetrating peptides as an innovative approach for drug delivery; then, present and the future", Journal of Pharmaceutical Investigation, 46: 205-220 (2016).
Extended European Search Report, issued Mar. 22, 2019 in corresponding European Patent Application No. 18197651.5.
Office Action issued May 8, 2021 in corresponding Chinese Patent Application No. 201880020127.6, with English Translation, 14 pages.
Langel, Ülo et al., "Cell-Penetrating Peptides: Methods and Protocols" (Chinese) World Publishing Corporation, 2016, pp. 1-13.
Kannan, Vinayagam et al., "Effect of sucrose as a lyoprotectant on the integrity of paclitaxel-loaded liposomes during lyophilization", Journal of Liposome Research, Dec. 23, 2014, vol. 25, No. 4, pp. 270-278.

(Continued)

*Primary Examiner* — Robert A Wax
*Assistant Examiner* — John W Lippert, III
(74) *Attorney, Agent, or Firm* — Wenderoth, Lind & Ponack, L.L.P.

(57) ABSTRACT

The present invention relates to a method of making an oral dosage form comprising the steps of reacting at least one cell penetrating peptide (CPP), purifying CPP-lipid conjugates, processing a lipid batch to obtain CPP-modified liposomes and incorporating a liposome lyophilisate into an oral dosage form. The present invention further relates to oral dosage forms and oral dosage forms for use in a therapeutic method.

17 Claims, 11 Drawing Sheets
Specification includes a Sequence Listing.

(56) References Cited

OTHER PUBLICATIONS

Lättig-Tünnemann, Gisela et al., "Backbone rigidity and static presentation of guanidinium groups increases cellular uptake of arginine-rich cell-penetrating peptides", Nature Communications, 2011, pp. 1-6.

Saw, Phei Er et al., "Efficient Liposomal Nanocarrier-mediated Oligodeoxynucleotide Delivery Involving Dual Use of a Cell-Penetrating Peptide as a Packaging and Intracellular Delivery Agent", Macromolecular. Rapid Communications, 2010, vol. 31, pp. 1155-1162.

Pantze, Silvia F. et al., "Matrix liposomes: A solid liposomal formulation for oral administration", Eur. J. Lipid Sci. Technol., 2014, vol. 116, pp. 1145-1154.

Zhang, Dongdong et al., "Cell-penetrating peptides as noninvasive transmembrane vectors for the development of novel multifunctional drug-delivery systems", Journal of Controlled Release, 2016, vol. 229, pp. 130-139.

International Search Report and Written Opinion of the International Searching Authority, issued Jun. 15, 2018 in corresponding International Patent Application No. PCT/EP2018/058464.

Office Action issued Aug. 19, 2020 in Russian Patent Application No. 2019134554.

Search Report issued Aug. 19, 2020 in Russian Patent Application No. 2019134554.

Chen, Yan et al., "Effect of cell-penetrating peptide-coated nanostructured lipid carriers on the oral absorption of tripterine", International Journal of Nanomedicine, 2012, vol. 7, pp. 4581-4591.

Fan, Tingting et al., "Design and evaluation of solid lipid nanoparticles modified with peptide ligand for oral delivery of protein drugs", European Journal of Pharmaceutics and Biopharmaceutics, 2014, vol. 88, pp. 518-528.

Fu, Han et al., "Tumor-Targeted Paclitaxel Delivery and Enhanced Penetration Using TAT-Decorated Liposomes Comprising Redox-Responsive Poly(Ethylene Glycol)", Journal of Pharmaceutical Sciences, 2015, vol. 103, pp. 1160-1173.

Khafagy, El-Sayed et al., "Oral biodrug delivery using cell-penetrating peptide", Advanced Drug Delivery Reviews, 2012, vol. 64, pp. 531-539.

Nischan, Nicole et al., "Covalent Attachment of Cyclic TAT Peptides to GFP Results in Protein Delivery into Live Cells with Immediate Bioavailability", Angew. Chem. Int. Ed., 2015, vol. 54, pp. 1950-1953.

Tseng, Yun-Long et al., "Translocation of Liposomes into Cancer Cells by Cell-Penetrating Peptides Penetratin and Tat: A Kinetic and Efficacy Study", Molecular Pharamacology, 2002, vol. 62, No. 4, pp. 864-872.

Sawant, Rupa R. et al., "Therapeutic delivery using cell-penetrating peptides CPPs: Tools for crossing the cell membrane and molecular mechanism", Eur. J. Nanomed. 2013, vol. 5, No. 3, pp. 141-158.

Qin, Yao et al., "Liposome formulated with TAT-modified cholesterol for improving brain delivery and therapeutic efficacy on brain glioma in animals", International Journal of Pharmaceutics, 2011, vol. 420, pp. 304-312.

Zhang, Xuanmiao et al., "Hepatitis B virus preS1-derived lipopeptide functionalized liposomes for targeting of hepatic cells", Biomaterials, 2014, vol. 35, pp. 6130-6141.

Paola Ringhieri et al., "The influence of liposomal formulation on the incorporation and retention of PNA oligomers", Colloids and Surfaces B: Biointerfaces, Sep. 1, 2016, vol. 145, pp. 462-469.

* cited by examiner

SEQUENCE LISTING

```
<160> NUMBER OF SEQ ID NOS: 9

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15
```

<210> SEQ ID NO 2
<211> LENGTH: 16
<212> TYPE: PRT
<213> ORGANISM: Human immunodeficiency virus type 1

<400> SEQUENCE: 2

```
Cys Gly Arg Lys Lys Arg Arg Gln Arg Arg Arg Pro Pro Gln Cys
1               5                   10                  15
```

<210> SEQ ID NO 3
<211> LENGTH: 27
<212> TYPE: PRT
<213> ORGANISM: Artificial sequence
<220> FEATURE:
<223> OTHER INFORMATION: artificially designed cell penetrating peptide

<400> SEQUENCE: 3

```
Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

<210> SEQ ID NO 4
<211> LENGTH: 9
<212> TYPE: PRT
<213> ORGANISM: Artificial sequence
<220> FEATURE:
<223> OTHER INFORMATION: artificially designed cell penetrating peptide

<400> SEQUENCE: 4

```
Arg Arg Arg Arg Arg Arg Arg Arg Arg
1               5
```

<210> SEQ ID NO 5
<211> LENGTH: 18
<212> TYPE: PRT
<213> ORGANISM: Mus musculus
<220> FEATURE:
<221> NAME/KEY: MISC_FEATURE
<222> LOCATION: (18)..(18)
<223> OTHER INFORMATION: K-amide

<400> SEQUENCE: 5

```
Leu Leu Ile Ile Leu Arg Arg Arg Ile Arg Lys Gln Ala His Ala His
1               5                   10                  15

Ser Lys
```

<210> SEQ ID NO 6
<211> LENGTH: 28
<212> TYPE: PRT
<213> ORGANISM: Homo sapiens
<220> FEATURE:
<221> NAME/KEY: MISC_FEATURE
<222> LOCATION: (28)..(28)
<223> OTHER INFORMATION: L-amide

<400> SEQUENCE: 6

```
Gly Trp Thr Leu Asn Ser Ala Gly Tyr Leu Leu Gly Lys Ile Asn Leu
1               5                   10                  15

Lys Ala Leu Ala Ala Leu Ala Lys Ile Ser Ile Leu
            20                  25
```

<210> SEQ ID NO 7
<211> LENGTH: 27
<212> TYPE: PRT

```
<213> ORGANISM: Human immunodeficiency virus

<400> SEQUENCE: 7

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 8
<211> LENGTH: 10
<212> TYPE: PRT
<213> ORGANISM: Artificial sequence
<220> FEATURE:
<223> OTHER INFORMATION: artificially designed cell penetrating peptide

<400> SEQUENCE: 8

Arg Arg Arg Arg Arg Arg Arg Arg Arg Cys
1               5                   10

<210> SEQ ID NO 9
<211> LENGTH: 10
<212> TYPE: PRT
<213> ORGANISM: Artificial sequence
<220> FEATURE:
<223> OTHER INFORMATION: artificially designed cell penetrating peptide

<400> SEQUENCE: 9

Arg Arg Arg Arg Arg Arg Arg Arg Arg Lys
1               5                   10
```

METHOD OF MAKING ORAL DOSAGE FORMS

This invention relates to methods of making oral dosage forms, oral dosage forms and methods of using the oral dosage forms.

Oral dosage forms are known in the art. They include for example tablets, pills, capsules, liquids, gels, suspensions, effervescent formulations, pellets, chewing gums, lozenges, granules, thin films, sprays and powders. Oral intake of pharmaceutical dosage forms is very convenient, and improves therapy adherence.

According to the European Pharmacopoeia (Ph. Eur.) and other regulations oral dosage forms must have a certain uniformity of dosage units. It is required that "each unit in a batch of oral dosage forms must have an active substance content within a narrow range around the label claim" (Ph. Eur., 2.9.40). "Active substance content" means that the substance is present in the dosage unit in the required amount and chemically unchanged, e.g. not degraded, derivatized, or covalently bound to other molecules. In order to achieve this uniformity of dosage units methods of making oral dosage forms must take into account any factors that might influence the amount and chemical integrity of active substances in the final dosage unit. With increasing overall complexity of a method of making an oral dosage form, it will become more difficult to ensure the uniformity of active substance in the final product. Methods of making oral dosage forms that include chemical reactions, the presence of reactive excipients or the use of active substances with reactive functional groups will increase this complexity and make it more difficult for the manufacturer to guarantee uniformity of the final product, and to suppress chemical side reactions.

Oral dosage forms may contain active pharmaceutical ingredients (APIs). Among the most relevant and commercially successful APIs are peptides and proteins, including for example antibodies and enzymes. These APIs are comprised of a plurality of amino acids that form a peptide chain. Many amino acids have reactive functional groups in their side chains. For example, cysteine has a thiol group, or lysine carries an amino group in its side chain. Other amino acids have further reactive functional groups in their side chains. Because of the diversity of side chain reactive groups in peptide and protein APIs a plurality of side reactions might occur. Making oral dosage forms with these kinds of APIs is particularly difficult because they are prone to unwanted side reactions that reduce the amount of unchanged API in the dosage form and affect product uniformity. Peptides and proteins that have undergone unwanted side reactions may form immunogenic products that may cause potentially fatal allergic reactions in a subject.

On the other hand, peptides and proteins require complex dosage forms to ensure oral bioavailability. This is particularly true for peptides with significant molecular size, such as polypeptides and proteins. Complex dosage forms require complex methods of production which again make it difficult to rule out unwanted side reactions and to ensure their stability until administration. The same applies to other APIs suffering from the same characteristics, i.e. reactive groups and low inherent bioavailability. In a complex method, it is difficult to control intermediate stages in such a way that no relevant side reactions occur. Therefore, it would be preferred to have methods that use intermediates that do not undergo any side reactions or other unwanted processes. It is an object of this invention to suggest a method of making oral dosage forms that overcome the mentioned problems of prior art methods. It is a further object to provide dosage forms with excellent uniformity.

SUMMARY OF THE INVENTION

In an aspect, the invention includes a method of making an oral dosage form, comprising the steps of
- a. reacting at least one CPP (cell penetrating peptide) with at least one first lipid to obtain CPP-lipid conjugates,
- b. purifying the CPP-lipid conjugates to obtain a purified CPP-lipid conjugate composition,
- c. preparing a lipid batch comprising at least
  - c1. a defined amount of the CPP-lipid conjugates and
  - c2. a defined amount of at least one non-CPP-conjugated second lipid,
- d. processing the lipid batch to obtain CPP-modified liposomes having a zeta potential of more than 2 mV and less than 10 mV,
- e. lyophilizing the CPP-modified liposomes to obtain a liposome lyophilisate,
- f. incorporating the liposome lyophilisate into an oral dosage form, wherein the amount of non-conjugated first lipid in the purified CPP-lipid conjugate composition is less than 5 mol % relative to the total molar amount of CPP-lipid conjugates in said composition.

The inventors found that the method allows for the production of oral dosage forms that are particularly resistant to side reactions during and after production and provide products with excellent uniformity and high reproducibility. Surprisingly, the oral dosage form obtainable by this method has excellent product uniformity.

In another aspect, the invention includes an oral dosage form, particularly an oral dosage form obtainable by the process of this invention, comprising CPP-modified liposomes, the liposomes having
- at least one CPP conjugated to a first lipid,
- at least one non-CPP-conjugated second lipid, and
- at least one pharmaceutically active ingredient (API), wherein the CPP-modified liposomes have a Z-average diameter in the range of from 50 nm to 250 nm, and a positive zeta potential, preferably in the range of from >2 mV to <10 mV.

It was found that these dosage forms have excellent uniformity, particularly when using peptides and proteins as the active substance. Apart from API content uniformity, uniformity is also confirmed by a low inter-batch variation in the liposomes' zeta potential and size.

According to this invention, "peptides" have at least one peptide bond, linking at least two amino acids together. "Polypeptides" have at least eight amino acids. "Proteins" have at least 30 amino acids. This invention is particularly useful for "polypeptides" and "proteins" as APIs.

The term "liposome" refers to artificially prepared vesicles composed of lipid bilayers. Liposomes can be used for delivery of APIs due to their unique property of encapsulating a portion of an aqueous solution inside a lipophilic bilayer membrane. Lipophilic compounds can be dissolved in the lipid bilayer, and in this way liposomes can carry both lipophilic and hydrophilic compounds. To deliver the molecules to sites of action, the lipid bilayer can fuse with other bilayers such as cell membranes, thus delivering the liposome contents.

The zeta potential can be determined by methods known in the art. The zeta potential may be determined after dilution of the liposomes to a lipid concentration of 0.95 mg/ml using a 50 mM phosphate buffer with a pH of 7.4. The default settings of the automatic mode of the Zetasizer Nano ZS from Malvern™ (Malvern Instruments Ltd., Worcestershire, United Kingdom) can be chosen as follows: number of measurements=3; run duration=10 s; number of runs=10; equilibration time=60 s; refractive index solvent 1.330; refractive index polystyrene cuvette 1.590; viscosity=0.8872 mPa s; temperature=25° C.; dielectric constant=78.5 F/m; backscattering mode (173°); automatic voltage selection; Smoluchowski equation.

DETAILED DESCRIPTION

The CPPs used in this invention may be selected from penetratin, TAT (transactivator of transcription), MAP (model amphiphatic peptide), polyarginines (including R3, R4, R5, R6, R7, R8, R9, R10, R11 and R12), pVEC, transportan, MPG, and combinations thereof. The CPPs used in this invention may be cyclized or linear, dimerized or un-dimerized. The CPPs may consist of the following sequences, or comprise the following sequences. Penetratin may include SEQ ID NO: 1; TAT may include SEQ ID NO: 2; MAP may include SEQ ID NO: 3; R9 may include SEQ ID NO: 4; pVEC may include SEQ ID NO: 5; transportan may include SEQ ID NO: 6; and/or MPG may include SEQ ID NO: 7. The listed CPPs include functional derivatives of the mentioned sequences. Functional derivatives include CPPs that consist of or comprise the above mentioned sequences, or sequences having at least 90%, or at least 95%, sequence identity therewith. Optionally, the functional derivative may include additional amino acids.

In an embodiment the CPPs used in this invention are positively charged and/or cyclized. Cyclized CPPs have the advantage of being less reactive and more stable than linear CPPs which is advantageous within the concept of this invention. Cyclic peptides may even be able to survive a gastric passage without enteric coating because they are more stable towards enzymatic cleavage than linear CPPs. As used herein, the term "cyclized" is not to be construed as relating to a peptide having one ring system only, i.e., the present invention is not limited to monocyclic peptides. Accordingly, the present invention includes cyclopeptides wherein two or more ring systems are covalently linked to each other. Furthermore, the cyclopeptides may also comprise amino acids which are not part of the ring system, i.e. the invention includes branched cyclopeptides. Preferably, the cyclopeptides are monocyclic peptides, and more preferably unbranched monocyclic peptides. Further, the CPPs can be composed of L-amino acids, D-amino acids, or mixtures thereof, wherein for linear CPPs, D-amino acids are preferred.

In an embodiment, the CPPs comprise a majority of lysine and/or arginine moieties, which have isoelectric points of around 9.5 and 11, respectively. Due to their additional amino or guanidine group, these two amino acids are positively charged under neutral and even under weakly basic conditions. Accordingly, a CPP mostly comprising moieties of said two specific amino acids is positively charged under neutral and weakly basic conditions as well. Herein, the term "majority" means that at least 50%, preferably at least 60%, more preferably at least 70%, and particularly preferably at least 80% of the amino acids forming the CPP molecule are lysine and/or arginine moieties. Thereby, it is ensured that the CPPs have a positive charge under neutral and weakly basic conditions, i.e., have an isoelectric point of more than 7. Therefore, in a specific embodiment of the present invention, the CPPs have an isoelectric point of more than 7.0, preferably of more than 7.5, more preferably of more than 8.0 and particularly preferably of more than 8.5. In this context, the isoelectric point of the CPP is the arithmetic mean of the isoelectric points of the amino acids forming the CPP.

In a specific embodiment of the present invention, the CPPs comprise between 2 to 19, preferably between 3 to 16, more preferably between 4 to 14, and particularly preferably between 6 to 12 arginine moieties as well as one or more moieties selected from the group consisting of tyrosine, threonine, serine, lysine, aspartic acid, glutamic acid, glutamine, asparagine and cysteine. For example, the CPP may comprise nine arginine moieties and one cysteine moiety in a ring system, and are referred to as a cyclic cysteine R9 derivative (such as SEQ ID NO: 8; RRRRRRRRRC). Another preferred example is a cyclopeptide comprising nine arginine moieties and one lysine moiety in the ring system, which is referred to as cyclic R9K derivative (SEQ ID NO: 9; RRRRRRRRRK).

The CPPs of this invention include dimerized CPPs, wherein homo- and heterodimers are within the scope of this disclosure. Dimerization of CPPs can be effected by any means known in the art. In a particular embodiment, CPPs are dimerized via the tripeptide KAK.

The amino acids forming the cyclopeptides are not limited to proteinogenic amino acids. Herein, the amino acids may be selected from any amino acids known in the art, and may include the respective D-enantiomer, L-enantiomer, or any mixture thereof.

The CPPs may be present in the CPP-modified liposomes in an amount of at least 0.05 mol %, at least 0.1 mol %, or at least 0.2 mol % relative to the total amount of lipid, i.e. first lipid plus second lipid, in the liposome. A minimum amount of CPP is considered necessary to improve membrane penetration. However, if a maximum amount of CPP is exceeded, unwanted side reactions may occur, content uniformity, homogeneity and liposome stability will decrease. Therefore, the maximum amount may be limited to 4 mol %, 2.5 mol %, or 1.5 mol % relative to the total amount of lipid, i.e. first lipid plus second lipid, in the liposome.

According to this invention the CPP is conjugated to at least one first lipid to obtain CPP-lipid conjugates. The first lipid may be selected from the group consisting of steroids (including cholesterol and its derivatives), fatty acids, fatty alcohols, fatty amines, hydrocarbons with carbon chain lengths of at least eight carbon atoms, phospholipids, sphingolipids, ceramides, glycolipids, etherlipids, carotenoids, glycerides and combinations thereof. Conjugation may include forming a covalent bond. The hydrocarbons preferably comprise at least one activating group for chemical coupling, such as maleimide active ester, amine alcohol, halogenide, thiol, ketone or aldehyde, triple and/or double carbon bonds.

In an embodiment the fatty acids, fatty amines, fatty alcohols and/or hydrocarbons may have carbon chain lengths of from 8 to 24 carbon atoms, preferably from 14 to 20 carbon atoms, or from 16 to 20 carbon atoms. The fatty acids, fatty amines, fatty alcohols and/or hydrocarbons may be saturated or unsaturated. Saturated compounds have the advantage of being chemically more stable than the unsaturated ones.

In an embodiment the phospholipids may be synthetic, semi-synthetic or natural phospholipids, or combinations thereof. Preferred phospholipids include phosphatidylcholines, phosphatidylethanolamines, phosphatidylinosites, phosphatidylserines, cephalines, phosphatidylglycerols, lysophospholipids, and combinations thereof. Preferred first lipids may be selected from TfpPEG13-DSPE [(2R)-3-((((4, 46-dioxo-46-(2,3,5,6-tetrafluorophenoxy)-7,10,13,16,19, 22,25,28,31,34,37,40,43-tridecaoxa-3-azahexatetracontyl) oxy)(hydroxy)phosphoryl)oxy)propane-1,2-diyl distearate (PEG(13)-distearoylphosphatidylethanolamine-tetrafluorophenyl ester)]; Mal-PEG12-DSPE [(2R)-3-((((46-(2,5-dioxo-2,5-dihydro-1H-pyrrol-1-yl)-4,44-dioxo-7,10,13,16,19, 22,25,28,31,34,37,40-dodecaoxa-3,43-diazahexatetracontyl)oxy)(hydroxy)phosphoryl)oxy) propane-1,2-diyl distearate]; 1,2-dioleoyl-sn-glycero-3-phosphoethanolamine-N-[4-(p-maleimidomethyl) cyclohexane-carboxamide] (sodium salt); 1,2-Dipalmitoyl-snGlycero-3-Phosphothioethanol (Sodium Salt); 1,2-dioleoyl-sn-glycero-3-phosphoethanolamineN-(succinyl) (sodium salt); 1,2-distearoyl-sn-glycero-3-phosphoethanolamine-N-[maleimide(polyethylene glycol)-2000] (ammonium salt); and combinations thereof.

In an embodiment the first lipid is activated. Activation of the first lipid may facilitate reaction of the CPP with the first lipid during CPP-lipid conjugate formation. An activated first lipid includes lipids that comprise an activating group. An activating group may be a group that has a greater reactivity towards the CPP than the lipid without the activating group. Suitable activating groups include activated polymeric groups (molecular weight more than 1,000 g/mol) and small molecule activating groups (molecular weight up to 1,000 g/mol).

Activated polymeric groups may include polyethylene glycol (PEG) covalently linked to one or more groups selected from a maleimide group (Mal), active esters, such as N-hydroxy succinimide (NHS), tetra fluorophenol (Tfp), and para-nitrophenol esters; amines, alcohols, ketones, aldehydes, thiols, halides, triple and double carbon bonds, and combinations thereof. Thus, an activating group may comprise a polymeric part and a reactive group covalently coupled to each other so that the polymeric part links the reactive group to the lipid. Exemplary activated polymeric groups include SM(PEG)$_{24}$ (PEGylated, long-chain SMCC crosslinker), SMCC (succinimidyl-4-(N-maleimidomethyl) cyclohexane-1-carboxylate)-linker, 6-maleimido hexanoic acid linker, and combinations thereof. The length of the polymeric part may influence liposome properties such as size and PDI. Accordingly, a preferred PEG polymeric part of an activated polymeric group may have a length of 8 to 50 individual PEG units.

Preferred activated first lipids include Tfp-PEG$_{13}$-DSPE [(2R)-3-((((4,46-dioxo-46-(2,3,5,6-tetrafluorophenoxy)-7, 10,13,16,19,22,25,28,31,34,37,40,43-tridecaoxa-3-azahexatetracontyl)oxy)(hydroxy)phosphoryl)oxy)propane-1,2-diyl distearate (PEG(13)-distearoylphosphatidylethanolamine-tetrafluorophenyl ester)]; Mal-PEG$_{12}$-DSPE [(2R)-3-((((46-(2,5-dioxo-2,5-dihydro-1H-pyrrol-1-yl)-4,44-dioxo-7,10, 13,16,19,22,25,28,31,34,37,40-dodecaoxa-3,43-diazahexatetracontyl)oxy)(hydroxy)phosphoryl)oxy) propane-1,2-diyl distearate]; 1,2-dipalmitoyl-sn-glycero-3-phosphoethanolamine-N-[4-(p-maleimidomethyl)cyclohexane-carboxamide] (sodium salt); 1,2-dioleoyl-sn-glycero-3-phosphoethanol-amine-N-[4-(p-maleimidomethyl)cyclohexanecarboxamide] (sodium salt); DSPE-PEG(2000) Maleimide (1,2-distearoyl-sn-glycero-3-phosphoethanolamine-N-[maleimide(polyethylene glycol)-2000] (ammonium salt)); and combinations thereof.

The second lipid may be selected from the group consisting of steroids (including cholesterol and its derivatives), fatty acids, fatty alcohols, fatty amines, hydrocarbons with carbon chain lengths of at least eight carbon atoms, sphingolipids, ceramides, glycolipids, etherlipids, carotenoids, glycerides, phospholipids, and combinations thereof.

In an embodiment the fatty acids, fatty amines, fatty alcohols and/or hydrocarbons may have carbon chain lengths of 8 to 24 carbon atoms, preferably from 14 to 22 carbon atoms, or from 16 to 20 carbon atoms. The fatty acids, fatty amines, fatty alcohols and/or hydrocarbons may be saturated or unsaturated. Saturated compounds have the advantage of being chemically more stable than the unsaturated ones.

In an embodiment the phospholipids may be synthetic, semi-synthetic or natural phospholipids, or combinations thereof. Preferred phospholipids include phosphatidylcholines, phosphatidylethanolamines, phosphatidylinosites, phosphatidylserines, cephalines, phosphatidylglycerols, lysophospholipids, and combinations thereof.

The second lipid may be the same as the first lipid, or different. In preferred embodiments, the second lipid is different from the first lipid. The difference may include that at least one, or all of the second lipids, do not have any activating group, i.e. the second lipids may be un-activated.

This aids in achieving one of the objectives of this invention to suppress any side reactions that might otherwise occur during the method.

Preferred combinations of second lipids include at least 50 mol %, at least 60 mol % or at least 70 mol % (relative to the total amount of second lipids) of at least one phospholipid. The amount of these lipids may be limited to a maximum of 99 mol %, or 97 mol % or 95 mol % relative to the total amount of second lipids. Alternatively or additionally, the second lipids may include an amount of steroids, such as cholesterol, which may range from 1 mol % to 20 mol %, or from 4 mol % to 12 mol % relative to the total amount of second lipid.

The CPP-lipid conjugates of this invention may have the following general structure:

$$FL-AG-CPP \qquad \text{(Formula I)}$$

In this formula, FL represents the first lipid, AG represents an optional activating group, and CPP represents the cell penetrating peptide. The hyphens represent covalent bonds. In other words, the CPP-lipid conjugate comprises the first lipid covalently attached to the CPP, wherein the covalent bond may optionally be achieved via an activating group, or directly without any activating group or other intermediate group in between.

Preferred CPP-lipid conjugates have molecular weights in the area of 1,000 to 10,000 g/mol, preferably from 1,200 to 5,000 g/mol, or from 1,500 to 3,500 g/mol. The relative weight amount of CPP-lipid conjugates in the CPP-modified liposomes may be in the area of 1 to 25 wt % relative to the total weight of the CPP-modified liposome. Preferred lower limits include 2 wt %, 3 wt % and 5 wt %. Preferred upper limits include 20 wt %, 15 wt % and 10 wt %.

The step of reacting at least one CPP with at least one first lipid to obtain CPP-lipid conjugates may include preparing a mixture of at least one CPP with at least one first lipid in a reaction vessel. The mixture may include a liquid medium.

The reaction mixture may include a molar excess of CPP over first lipid. In embodiments, the molar proportion of CPP exceeds the molar proportion of first lipid in the reaction mixture by a factor of at least 1.5, preferably at least 2, or at least 2.5. Using an excess of CPP over first lipid reduces the amount of unreacted first lipid in the reaction mixture after the reaction. This has certain benefits. One is that the subsequent step of purifying the CPP-lipid conjugates to obtain a purified CPP-lipid conjugate composition requires less effort. This is because the physicochemical difference between CPP and CPP-lipid conjugates is greater than the physicochemical difference between first lipid and CPP-lipid conjugates. Thus, it is easier to separate unreacted CPP from CPP-lipid conjugates than it is to separate unreacted first lipid from CPP-lipid conjugates. Furthermore, unreacted first lipid has a tendency to react with amino acids, particularly if the first lipid carries at least one activating group to further facilitate reactions of the first lipid with the CPP. Having relevant amounts of unreacted first lipid in the product, the risk of an API undergoing unwanted reactions with the first lipid will increase. This is particularly true for peptide and protein APIs.

It has been found that reacting CPP and first lipid in a separate reaction, i.e. before liposomes are formed, results in more uniform oral dosage forms that contain exactly predetermined amounts of CPP. Also, the method is economically more efficient because less CPP and first lipid are used. In the prior art CPP-modified liposomes are produced by reacting CPPs with liposomes, i.e. the reaction of CPP with lipid is carried out after the liposomes have been produced. In this invention, CPP-lipid conjugates are produced first, and then liposomes are formed that contain the pre-produced CPP-lipid conjugates. This ensures that the amount of CPP-lipid conjugates present in the liposomes can be exactly tuned as necessary for the intended purpose. As mentioned above, the amount of CPP (and of CPP-lipid conjugates) in the liposomes should be well balanced so that the positive effect on membrane penetration of the API, particularly on peptides and proteins, is maximized whereas the stability and uniformity of the liposomes is not put at risk due to a maximum amount of CPP being exceeded. It has been found that by reacting CPP and first lipid in a separate reaction before liposomes are formed, a higher amount of CPP can be used in the liposomes without running the risk of exceeding the maximum amount allowed for the respective liposome. Thus, this particular sequence of method steps increases the positive effect of CPP on oral bioavailability without risking negative effects on liposome uniformity and stability. Particularly, liposome stability during freeze-drying/lyophilisation is very high for the liposomes of this invention.

Preferably, the step of reacting at least one CPP with at least one first lipid to obtain CPP-lipid conjugates comprises forming a solution of CPP and first lipid in a first liquid medium. Suitable first liquid media include organic solvents, such as an organic solvent selected from aromatic and aliphatic alcohols, halogenated or non-halogenated alkanes, carboxylic acid esters and amides, and combinations thereof.

The method of this invention includes the step of purifying the CPP-lipid conjugates in order to obtain a purified CPP-lipid conjugate composition. This step is important to achieve one of the objectives of this invention, namely to increase uniformity of the oral dosage forms and to avoid side reactions, particularly reactions of lipid with API. As mentioned, uniformity of oral dosage forms includes that the API is not chemically changed during production and storage. The method includes the step of reacting a CPP with a first lipid. Hence, the first lipid has certain reactivity towards peptides. It has been found that unwanted side reactions can be reduced, if the CPP-lipid conjugates are purified after their formation. Preferably, after purification the amount of non-conjugated first lipid in the CPP-lipid conjugate composition is less than 5 mol % relative to the total molar amount of CPP-lipid conjugates in said composition. In preferred embodiments, the amount of non-conjugated first lipid in said composition is less than 3 mol %, less than 1 mol %, or even less than 0.5 mol %. By reducing the amount of non-conjugated first lipid, and thereby inherently reducing the amount of reactive first lipid, the amount of unwanted side reactions is reduced. In preferred embodiments, not only the purified CPP-lipid conjugate composition has these limited amounts of non-conjugated first lipid, but also the final CPP-modified liposomes that can be used in the oral dosage form.

Purification of the CPP-lipid conjugates can be done for example by HPLC, size exclusion chromatography, ion exchange chromatography, or other suitable methods known to those skilled in the art. Generally, very careful purification of the conjugates is necessary in order to separate non-conjugated first lipid from CPP-conjugated first lipid because these two substances have very similar physicochemical properties. During purification of the CPP-lipid conjugates any unreacted CPP should also be removed, which is easily achieved because of the physicochemical differences between CPP and lipids.

In preferred embodiments, purifying the CPP-lipid conjugates to obtain a purified CPP-lipid conjugate composition includes the steps of b1. separating CPP-lipid conjugates from non-conjugated first lipid, and b2. optionally separating CPP-lipid conjugates from non-conjugated CPP and/or conjugates carrying more than one CPP.

Steps b1 and b2 need not be carried out in separate steps, but can be carried out together with an appropriate method, such as HPLC.

The method of this invention includes the step of preparing a lipid batch comprising c1. a defined amount of the CPP-lipid conjugates and c2. a defined amount of at least one non-CPP-conjugated second lipid.

After purification the purified CPP-lipid conjugate composition is used to make a lipid batch together with the second lipid. The second lipid may remain unconjugated. It is an advantage of the present invention that a defined amount of CPP-lipid conjugate can be used to make the lipid batch. In the prior art the exact amounts of CPP-lipid conjugates in the final product remain undefined because the conjugates are formed after liposome preparation. In preferred embodiments, the weight ratio of non-CPP-conjugated second lipid to CPP-lipid conjugates is at least 7 to 1, more preferably at least 15 to 1 and most preferably at least 20 to 1. The benefit of using a defined amount of CPP-lipid conjugates in the lipid batch is that the method can use an amount of CPP that is very close to the maximum useful amount without running the risk of adding too much CPP, which might increase the risk of unwanted side effects of the dosage form. Choosing the above-mentioned ratios has shown to yield stable liposomes for further processing during the method of this invention.

In certain embodiments, the step of preparing a lipid batch comprises forming a mixture (e.g. a solution) of CPP-lipid conjugates and non-CPP-conjugated second lipids in a second liquid medium. Preferred second liquid medium is selected from aromatic and aliphatic alcohols, halogenated or non-halogenated alkanes, carboxylic acid esters and amides, and combinations thereof. The first and second liquid medium may be the same or different.

As a next step the method includes processing the lipid batch to obtain CPP-modified liposomes having a zeta potential of more than 2 mV and less than 10 mV. Generally, a higher zeta potential is useful to increase a liposome's property to facilitate membrane penetration of APIs. However, if the zeta potential is too high, liposomes will not be stable and less homogeneous. It is one of the benefits of this invention that zeta potential can be tuned to be close to the maximum limit without risking stability. Depending on the exact kind of lipids and CPP used for the liposome, the exact value for the zeta potential can vary. In certain embodiments, the zeta potential is up to 8 mV, or up to 6 mV. The method of this invention has the advantage that variations of the zeta potential between different batches of liposomes are very small.

In preferred embodiments, processing the lipid batch to obtain CPP-modified liposomes includes high pressure homogenization, extrusion, ethanol injection and/or dual asymmetric centrifugation (DAC). These processes are known in the art.

In an embodiment, the step of processing the lipid batch to obtain CPP-modified liposomes includes
 d1. incorporating at least one pharmaceutically active ingredient into the CPP-modified liposomes.

This invention is particularly useful for proteins and peptides, such as polypeptides having at least eight amino acids. The method of this invention allows for a good incorporation efficiency even of larger molecules. Without wishing to be bound by this theory, the liposomes have good membrane fluidity based on the composition of the membrane and the method of their production. Membrane fluidity is considered relevant for the incorporation of APIs, for the lyophilisation, and for the delivery of APIs across membranes. Any components that might have a negative influence on membrane fluidity should therefore be avoided. Such components include tetraether lipids. The amount of tetraether lipids in the liposomes is preferably limited to amounts of less than 1 mol % relative to the total amount of lipids in the liposomes. Preferably, this amount is limited to less than 0.1 mol % or even less than 0.01 mol %.

It is an important aspect of this invention that the liposomes are already CPP-modified, when the API is incorporated. In prior art methods that modify liposomes with CPPs at later stages, increased temperatures are needed that will negatively affect API stability. Also, activated lipids might covalently modify the API in prior art methods. Thus, the inventive method avoids API deterioration which is very useful for peptides and proteins.

APIs useful within this invention include proteins and peptides, particularly polypeptides. Preferred APIs have molecular weights in the range of from 1,000 to 150,000 g/mol, preferably from 10,000 to 100,000 g/mol, or from 30,000 to 80,000 g/mol. Preferred APIs may be selected from anti-cancer agents (e.g. rituximab, trastuzumab, nivolumab); immune-modulatory agents (e.g. adalimumab, eternacept, cytokines, interferons, glatiramer acetate); hormones such as insulin, GLP-1 analogues, somatostatin and its analogues, hGh, and octreotide; glycopeptide antibiotics e.g. vancomycin and daptomycin; peptide drugs for hepatitis treatment such as Myrcludex B; and peptides and antibodies acting on cellular receptors such as glucagon, leuprolide, octreotide, vasopressin, and cetuximab.

Suitable APIs include, without limitation, vancomycin, glatiramer acetate, Myrcludex B, octreotide, insulins, and liraglutide, as well as other GLP (glucagon-like peptide)-analogues such as exenatide, lixisenatide, albiglutide, dulaglutide, taspoglutide, and semaglutide, and antibodies (e.g. etanercept; pegfilgrastim; adalimumab, infliximab, rituximab, epoietin alfa, tratuzumab, ranibizumab, beta-interferon, omalizumab). Other examples include pharmaceutically active agents selected from the group consisting of hormones, such as human growth hormone, growth hormone releasing hormone, growth hormone releasing peptide, interferons, colony stimulating factors, interleukins, macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin and fragment polypeptides thereof, apolipoprotein-E, erythropoietin, factor VII, factor VIII, factor IX, plasminogen activating factor, urokinase, streptokinase, protein C, C-reactive protein, renin inhibitor, collagenase inhibitor, superoxide dismutase, platelet-derived growth factor, epidermal growth factor, osteogenic growth factor, bone stimulating protein, insulin, atriopeptin, cartilage inducing factor, connective tissue activating factor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, monoclonal or polyclonal antibodies against various viruses, bacteria, or toxins, virus-derived vaccine antigens, cyclosporine, rifampycin, lopinavir, ritonavir, telavancin, oritavancin, dalbavancin, bisphosphonates, itraconazole, danazol, paclitaxel, naproxen, capsaicin, albuterol sulfate, terbutaline sulfate, diphenhydramine hydrochloride, chlorpheniramine maleate, loratidine hydrochloride, fexofenadine hydrochloride, phenylbutazone, nifedipine, carbamazepine, betamethasone, dexamethasone, prednisone, hydrocortisone, 17 beta-estradiol, ketoconazole, mefenamic acid, beclomethasone, alprazolam, midazolam, miconazole, ibuprofen, ketoprofen, prednisolone, methylprednisone, phenytoin, testosterone, flunisolide, diflunisal, budesonide, fluticasone, glucagon-like peptide, C-Peptide, calcitonin, lutenizing hormone, prolactin, adrenocorticotropic hormone, leuprolide, interferon alpha2b, interferon beta-la, sargramostim, aldesleukin, interferon alpha-2a, interferon alpha-n3alphaproteinase inhibitor, etidronate, nafarelin, chorionic gonadotropin, prostaglandin E2, epoprostenol, acarbose, metformin, desmopressin, cyclodextrin, antibiotics, antifungal drugs, steroids, anticancer drugs, analgesics, anti-inflammatory agents, anthelmintics, anti-arrhythmic agents, penicillins, anticoagulants, antidepressants, antidiabetic agents, antiepileptics, antihistamines, antihypertensive agents, antimuscarinic agents, antimycobacterial agents, antineoplastic agents, CNS-active agents, immunosuppressants, antithyroid agents, antiviral agents, anxiolytic sedatives, hypnotics, neuroleptics, astringents, beta-adrenoceptor blocking agents, blood products and substitutes, cardiacinotropic agents, contrast media, corticosteroids, cough suppressants, expectorants, mucolytics, diuretics, dopaminergics, antiparkinsonian agents, haemostatics, immunological agents, lipid regulating agents, muscle relaxants, parasympathomimetics, parathyroid calcitonin, prostaglandins, radiopharmaceuticals, sex hormones, anti-allergic agents, stimulants, anoretics, sympathomimetics, thyroid agents, vasidilators, xanthines, heparins, therapeutic oligonucleotides, somatostatins and analogues thereof, and pharmacologically acceptable organic and inorganic salts or metal complexes thereof.

The method of this invention includes the step of lyophilizing the CPP-modified liposomes to obtain a lyophilisate. Preferred lyophilisates have limited water content, preferably of not more than 5 wt %, or less than 3 wt %. The water content can be determined by Karl-Fischer-titration or automated systems such as Water Content Analyzer. Compared to liquid formulations of CPP-modified liposomes freeze-dried/lyophilized liposomes have better long-term stability. One important property of the liposomes of this invention is that uniformity of the liposomes is not significantly changed during lyophilisation. On the one hand, this property is influenced by the method of this invention as described above. On the other hand, the choice and more particularly the amount of lyoprotector is important to achieve this property.

The step of lyophilizing the CPP-modified liposomes to obtain a liposome lyophilisate may include:
  e1. preparing a mixture of the CPP-modified liposomes and at least one lyoprotector.

It has been shown that there is an optimum amount range for lyoprotector in relation to the amount of lipid in the mixture. Preferably, the amount of lyoprotector ranges from 0.01 to 2 g lyoprotector per gram of lipid, preferably from 0.02 to 1 g per gram lipid, or from 0.03 to 0.5 g per gram of lipid. In preferred embodiments, a minimum value is at least 0.03 g per 1 g of lipid. A maximum value may be 0.3, 0.2 or 0.1 g lyoprotector per g of lipid. In this context, "lipid" refers to the total amount of conjugated, or un-conjugated first and second lipid in the composition. It was found that a lower amount of lyoprotector will destabilize liposomes, reduce the Z-average value and thereby affect product uniformity. Higher amounts of the amount of lyoprotector are not desirable because higher amounts would not further increase the positive effects, and many lyoprotectors are not suitable for diabetics so that the amount should be limited. Thus, the amount of lyoprotector should preferably not exceed 0.5 g per 1 g of lipid. In embodiments, these limitations concerning the amount of lyoprotector relative to the amount of lipid apply to the oral dosage forms and liposomes as well.

The lyoprotector may be selected from the saccharides, preferably monosaccharides or disaccharides, including sugars and sugar alcohols. The lyoprotector may be selected from sucrose, mannitol, glucose, trehalose, lactose, palatinose and combinations thereof.

In preferred embodiments, the zeta potential and/or Z-average of the CPP-modified liposomes does not change significantly after reconstitution of the liposome lyophilisate in water. Particularly, the change of zeta potential, and/or its Z-average is not more than 5%, preferably not more than 3% compared to the respective value before lyophilisation. This shows that the liposomes obtained by the method of this invention are particularly stable, and have excellent membrane fluidities.

The mixture of CPP-modified liposomes and lyoprotector may be prepared in a solvent. The solvent may be aqueous, such as solvents comprising at least 50 wt % water, or at least 75 wt %, or at least 95 wt % of water. The solvent may be buffered to pH values from 2 to 12, or from 4 to 10, or from 5.5 to 8.5. In preferred embodiments, the solvent is PBS (phosphate buffered saline).

Finally, lyophilisation includes freeze drying of the mixture of CPP-modified liposomes and lyoprotector as per se known from the art.

The step of incorporating the liposome lyophilisate may include, without limitation, the preparation of tablets, pills, capsules, pellets, liquids (including suspensions), powder, thin films, effervescent formulations, pastes, lozenges, chewing gums, gels, sprays or granules.

According to the present invention, the solid oral dosage forms may further comprise at least one pharmaceutically acceptable excipient, and/or at least one protease inhibitor, and/or at least one lipase inhibitor. These substances can be incorporated into the dosage form. The mentioned substances can be present in the inner lumen of the liposomes, in the liposomes' lipid double layer (e.g. forming a part of the double layer by covalent or non-covalent attachment), or outside of the liposomes (e.g. in other parts of the dosage form). Preferably, said at least one pharmaceutically acceptable excipient is selected from the group consisting of sorbitan monostearate, tripalmitin, cetyl palmitate, alginate, ethyl oleate, C8 triglycerides, C10 triglycerides, cellulose, disaccharides, monosaccharides, oligosaccharides, magnesium stearate, corn starch, citric acid, tartaric acid, acid salts of amino acids, and combinations thereof. Furthermore, said at least one protease inhibitor is preferably selected from the group consisting of aprotinin, soybean trypsin inhibitor, bacitracin, sodium glycocholate, bestatin, leupeptin, cystatin, camostat mesilate, and combinations thereof. Furthermore, said at least one lipase inhibitor is preferably selected from the group, consisting of orlistat, lipstatin, chitin, chitosan, saponin, flavonoid glycoside, polyphenole, ebelacton A and B, esterastin, valilactone, panclicine, proanthocyanidin, vibralactone, and combinations thereof.

The CPP-modified liposomes have the advantage of being very stable and uniform. Preferably, they have a Z-average diameter in the range of from 50 nm to 250 nm. The term and determination of the Z-average diameter is known to the skilled person. This value is defined in ISO 22412:2008. In preferred embodiments, the CPP-modified liposomes have a minimum Z-average diameter of 75 nm, or more preferred of 100 nm. The maximum Z-average diameter may be limited to 225 nm. The PDI of the CPP-modified liposomes may be less than 0.5, less than 0.45, less than 0.4 or less than 0.3.

In preferred embodiments, the zeta potential and/or Z-average of the CPP-modified liposomes does not change significantly after reconstitution of the liposome lyophilisate in water. Particularly, the change of zeta potential, and/or Z-average changes by not more than 5%, preferably not more than 3% compared to the respective amount before lyophilization. This shows that the liposomes as obtained by the method of this invention are particularly stable.

An API may be embedded in the CPP-modified liposomes. Depending on its hydrophilicity, the API will be predominantly present inside the liposome, where the environment may be aqueous, or within the bilayer of the liposome, where the environment is more lipophilic. For proteins and polypeptides the API may be predominantly present within the liposome. In the liposome second lipids will form part of the double layer.

The CPPs may be present in the CPP-modified liposomes in an amount of at least 0.05 mol %, at least 0.1 mol %, or at least 0.2 mol % relative to the total amount of lipid, i.e. first lipid plus second lipid, in the liposome. A minimum amount of CPP is considered necessary to improve the membrane penetration of APIs. However, if a maximum amount of CPP is exceeded, unwanted side reactions may occur, content uniformity and liposome stability will decrease. Therefore, the maximum amount may be limited to 4 mol %, 2.5 mol %, or 1.5 mol % relative to the total amount of lipid, i.e. first lipid plus second lipid, in the liposome.

The CPP-modified liposomes in the oral dosage form may have a positive zeta potential, preferably in the range of from >2 mV to <10 mV. In embodiments, the zeta potential is up to 8 mV or up to 6 mV. Liposomes with this zeta potential have proven to be stable; they retain their zeta potential even after freeze drying and subsequent reconstitution.

Preferably, the amount of non-conjugated first lipid in the CPP-modified liposome is less than 5 mol % relative to the total molar amount of CPP-lipid conjugates in said liposome. In preferred embodiments, the amount of non-conjugated first lipid in said liposome is less than 3 mol %, less than 1 mol %, or even less than 0.5 mol %. By reducing the amount of non-conjugated first lipid, and thereby inherently reducing the amount of reactive first lipid, the amount of unwanted side reactions is reduced, making the liposome more stable against degradation.

This invention also relates to an oral dosage form comprising the CPP-modified liposomes described herein, having
- at least one CPP conjugated to a first lipid,
- at least one non-CPP-conjugated second lipid, and
- at least one pharmaceutically active ingredient (API),
wherein the CPP-modified liposomes have a Z-average diameter in the range of from 50 nm to 250 nm, and a positive zeta potential, preferably in the range of from >2 mV to <10 mV.

The oral dosage form may be obtainable by the method described herein.

The invention includes an oral dosage form, wherein the amount of non-conjugated first lipid in the CPP-modified liposomes is less than 5 mol %, preferably less than 3 mol %, relative to the total molar amount of CPP-lipid conjugates in the CPP-modified liposomes.

The oral dosage form is not particularly limited to a specific kind thereof. Solid oral dosage forms are preferred. In some embodiments, the oral dosage form is a gastro-resistant dosage form, such as an enteric coated form, which may protect the API from gastric juice after oral intake. The dosage form may be a tablet, a capsule, a powder, a granulate, a pellet, or a combination thereof.

A method of treatment according to this invention includes the step of administering to a subject in need thereof the oral dosage form of this invention containing an effective amount of API. The subject may be human. In embodiments, the oral dosage form of this invention is a composition for use in a therapeutic or diagnostic method.

EXAMPLES

Figure 1:
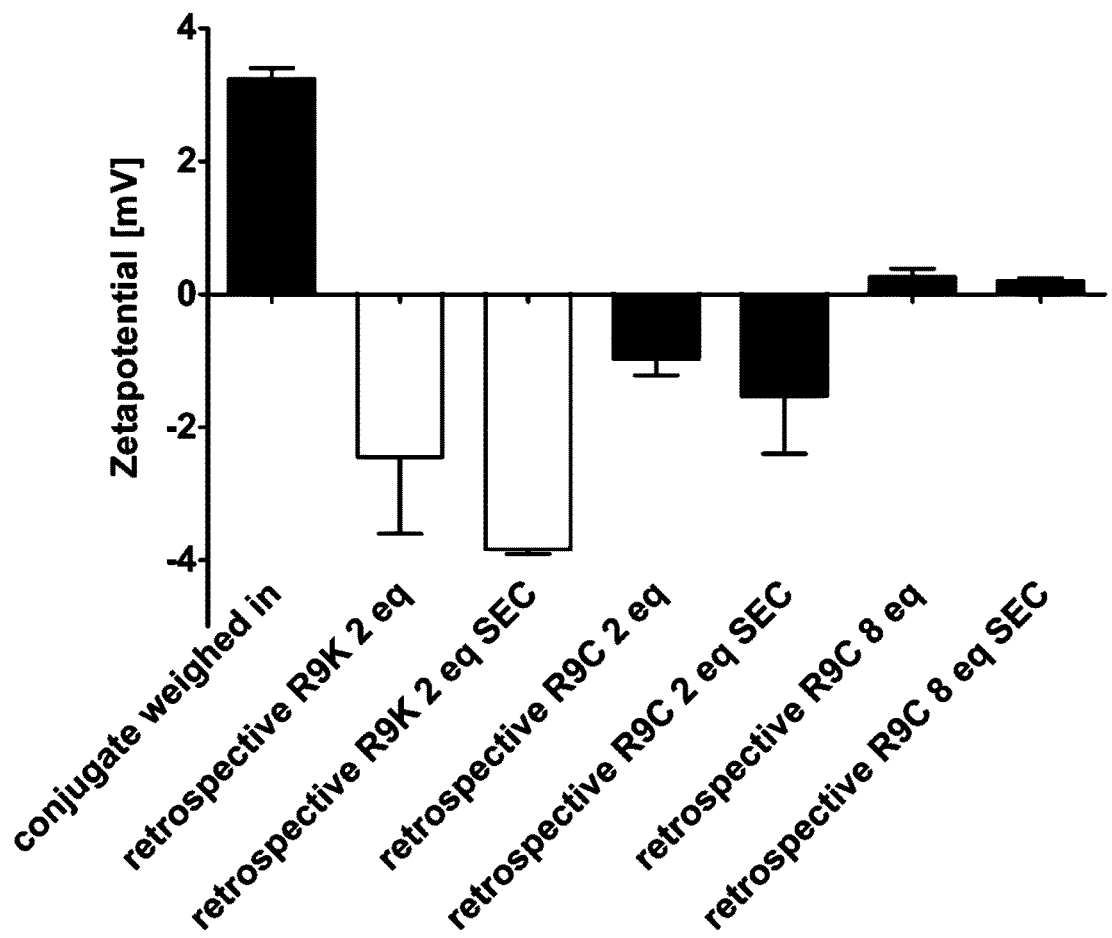
FIG. 1 Comparison of CPP-modified liposomes prepared according to this invention with CPP-modified liposomes obtained by coupling CPPs directly to the liposomes.

Synthesis of Cyclic R9-Peptides (R9C and R9K)

Peptide synthesis was carried out on a Chloro-(2'-chloro) trityl Polystyrene resin with a capacity of 0.89 mmol/g. Loading was done with 0.8 mmol of Fmoc-Lys(Boc)-OH or Fmoc-Cys(Trt)-OH per gram resin in DCM with 3 equivalents of DIPEA for 2 h. Excess 2-chlorotrityl-functions were quenched by MeOH-loading with a mixture of DCM/MeOH/DIPEA of 17:2:1. After removal of the Fmoc-protecting-group nine consecutive steps of coupling Fmoc-Arg(Pbf)-OH in DMF, with an excess of 7 equivalents fmoc-amino acid, 6.6 equivalents HBTU, and 4 equivalents DIPEA followed by Fmoc-group removal by treatment with 20% piperidine in DMF were performed. In between steps the resin was washed rigorously with DMF. Cleavage of the side chain protected peptide was achieved by a mixture of DCM/Trifluoroethanol/acetic acid of 7:2:1. The cleavage solution was co-evaporated with toluene three times on a rotary evaporator. The side chain protected peptide was dissolved in DMF in a concentration of 3 mg/ml. Cyclization was performed with 4 equivalents of PyAOP and DIPEA at RT overnight.

After stopping the reaction with water (3% v/v) the solution was concentrated to a fiftieth to hundredth of the starting volume and the side chain protected cyclo-peptide precipitated by pouring into cold tButyl-methylether. The precipitated protected cyclo-peptide was dried and subsequently deprotected with a mixture of 5% Dithioethanole in TFA. After precipitation with diethylether the cyclo-peptide was purified with HPLC using a Chromolithe® Performance RP-C18e column (100×3 mm). Water and acetonitrile containing 0.05% TFA were used as eluents with a flow rate of 2 ml/min.

Synthesis of the CPP-Lipid-Conjugates

To maleimido-PEG(12)-distearoylphosphatidylethanolamine (Iris Biotech) or PEG(13)-distearoylphosphatidylethanolamine-tetrafluorophenyl ester (Iris Biotech) dissolved in DMF in a concentration of 5 mg/ml 3 equivalents of CPP (cyclic R9-peptides) and 10 equivalents of DIPEA were added. The reaction mixture was stirred overnight at room temperature. The reaction mixture was diluted with a 1:2 mixture of ACN/H$_2$O and purification was performed via HPLC using a Chromolithe® Performance RP-C18e column (100×3 mm). Water and acetonitrile containing 0.05% TFA were used as eluents with a flow rate of 2 ml/min.

Preparation of Liposomes:

Preparation of Lipid Mixture:

First, respective lipids (EPC, cholesterol, maleimido-PEG (12)-distearoylphosphatidyl-ethanolamine, PEG(13)-distearoylphosphatidylethanolamine-tetrafluorophenyl ester) were dissolved in methanol or chloroform in order to obtain stock solutions (7-10 mg/ml). The CPP-lipid-conjugate was also dissolved in methanol in a concentration of 7 mg/ml.

The required amounts of each stock solution were mixed in respective ratios and the organic solvent evaporated by a nitrogen stream heated to 40° C.

The resulting lipid mixture was dried for 1 h in a freeze drier (AdVantage Plus XL-70, SP Scientific).

Dual Asymmetric Centrifugation:

Liposomes were prepared by dual asymmetric centrifugation using a SpeedMixer™ (DAC150.1 CM41, Hauschild Engineering GmbH & Co. KG, Hamm, Germany). Before liposomal preparation, 20 mg of glass beads (o 0.75-1 mm) were added to the lipid mixture (18 mg total lipid mass) in a 2 ml reaction tube. The liposomes were prepared by speed mixing at 300 rpm in a dual asymmetric centrifuge using a special vial holder. Two subsequent runs were performed (30 min and 5 min) after different amounts of phosphate buffered saline (PBS) or drug solutions (for drug-containing liposome preparation; 20 mg/ml for vancomycin; 1 mg/ml for insulin) were added (50 µl and 100 µl, respectively). This was followed by a third run with a duration of 5 min after 150 µl PBS was added.

The liposomal characteristics were determined by zetasizer measurements. Liposomes were purified by size exclusion chromatography (NAP5 columns) and the liposomal characteristics were determined again.

Coupling of the CPPs after Liposomal Preparation (Comparative)

Liposomes containing 1% of maleimido-PEG(12)-distearoylphosphatidylethanolamine (Iris Biotech) or PEG(13)-distearoylphosphatidylethanolamine-tetrafluorophenyl ester (Iris Biotech) were prepared. The required cyclic-CPP (cycR9C or cycR9K) was dissolved in PBS (0.5 to 2 mg), added to the liposomal suspension and incubated overnight (room temperature to 50° C.). The liposomal characteristics were determined by zetasizer measurements. Free CPP was removed by size exclusion chromatography (NAP5 columns) and the liposomal characteristics were determined again.

Zetasizer Measurements

The particle size, PDI and zeta potential of all liposomal formulations were determined at room temperature using a zetasizer Nano ZS from Malvern™ (Malvern Instruments Ltd., Worcestershire, United Kingdom). Size and PDI were measured after dilution to a lipid concentration of 0.076 mg/ml with a 10 mM phosphate buffer with a pH of 7.4 using the automatic mode. The zeta potential was determined after dilution to a lipid concentration of 0.95 mg/ml by a 50 mM phosphate buffer with a pH of 7.4. The default settings of the automatic mode of the zetasizer Nano ZS from Malvern™ (Malvern Instruments Ltd., Worcestershire, United Kingdom) were the following: number of measurements=3; run duration=10 s; number of runs=10; equilibration time=60 s; refractive index solvent 1.330; refractive index polystyrene cuvette 1.590; viscosity=0.8872 mPa s; temperature=25° C.; dielectric constant=78.5 F/m; backscattering mode (173°); automatic voltage selection; Smoluchowski equation.

Freeze-Drying:

In order to obtain a solid liposomal preparation, the liposomes were freeze-dries in a Virtis Advantage Plus XL-70 freeze-dryer. The main drying was carried out at −20° C. for 2 days followed by a secondary drying at 0° C. for at least 6 h. Sucrose in different amounts was used as lyoprotector. Briefly, the liposomes were prepared as described above and the required amount of sucrose was added. The liposomal suspension was partitioned into 50 µl aliquots and freeze-dried. In order to assess the quality of the freeze-dried products, the liposomes were rehydrated with 50 µl PBS and the size, z-average and PDI were determined.

DESCRIPTION OF FIGURES

Comparison of Zeta Potential Conjugates Vs. Coupling Post Liposomal Production (FIG. 1)

The highest zeta potential can be achieved by our conjugation and synthesis strategy. CPP coupling after the preparation of the liposomes does not lead to the same high zeta potential value, even if high excess of CPP is used. The results are shown in FIG. 1. It can be seen that the inventive method with the pre-synthesized conjugate weighed in for the liposome preparation yields very high zeta potential values in the area of 3.5 mV. Such high values for the zeta potential could not be reached with different amounts (eq=equivalents relative to first lipid) of CPP using conventional preparation techniques where the conjugates are synthesized after liposome preparation. Notably, using eight equivalents of R9C achieved only slightly positive zeta potentials.

Figure 2:
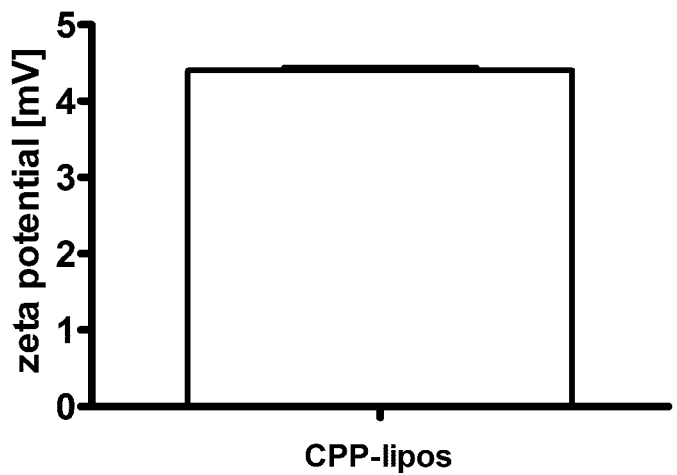
FIG. 2 Low variation of zeta potentials between same batches of liposomes prepared according to this invention.

Intra-Batch Variations of Zeta Potential (FIG. 2)

FIG. 2 shows that variations of zeta potential between samples of the same batch of liposomes prepared according to this invention is very small. The following table shows the underlying data:

| batch | zeta potential [mV] |
|---|---|
| 1 | 4.48 |
| 2 | 4.35 |
| 3 | 4.37 |

Figure 3:
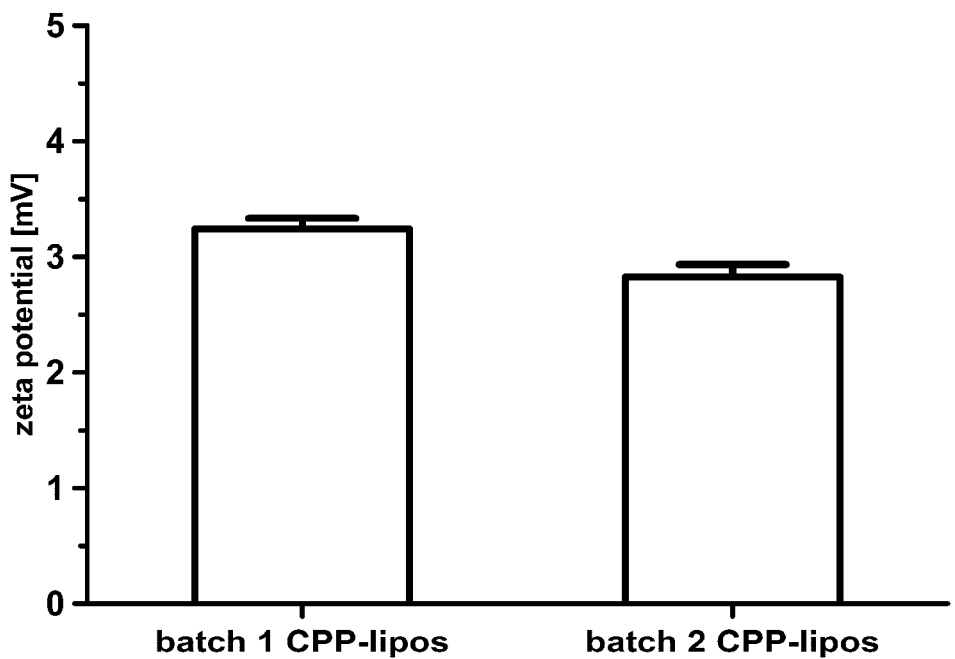
FIG. 3 Low variation of zeta potentials between different batches of liposomes prepared according to this invention.

Inter-Batch Variations of Zeta Potential (FIG. 3)

FIG. 3 shows that variations of zeta potential between different batches of liposomes prepared according to this invention is very small.

The Comparison of the zeta potential of two different liposomal production processes (batch 1 and 2) is shown. The figure strongly highlights the high reproducibility of the zeta potential by our production method.

Figure 4:
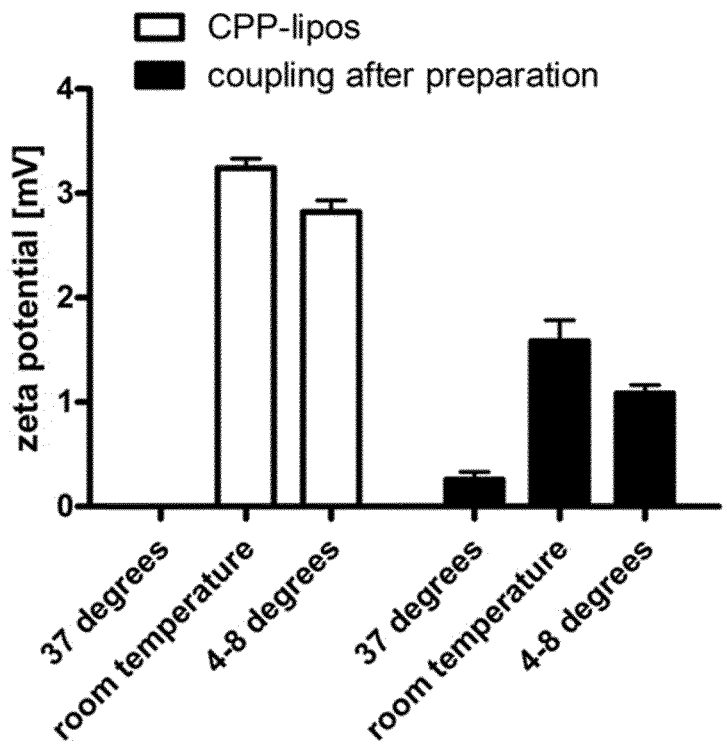
FIG. 4 Influence of temperature for different liposome preparation methods regarding liposomal characteristics.

Production of Liposomes is Independent of Temperature (FIG. 4)

Comparison of the zeta potential of the CPP-liposomes and liposomes by which the CPP was coupled after liposomal production. The incomplete coupling is clearly shown by the lower zeta potential. Therefore this graph demonstrates the high reproducibility of liposomal production with high and constant zeta potential by our method independent of the temperature during production.

Figure 5:
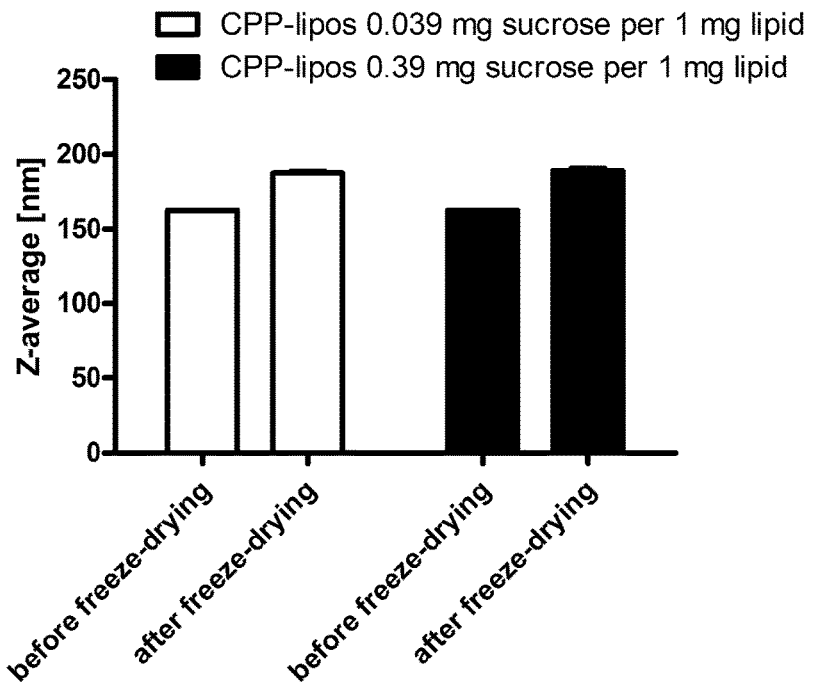
FIG. 5 Comparison of Z-average before and after the lyophilization process for different amounts of sucrose as lyoprotector.

Z-Average Pre- and Post Lyophilisation (FIG. 5)

Comparison of the Z-average of CPP-liposomes freeze dried with 0.039 m and 0.39 mg sucrose per 1 mg of lipid as lyoprotector. The successful lyophilisation is demonstrated by the constant Z-average before and after the freeze-drying process.

Figure 6:
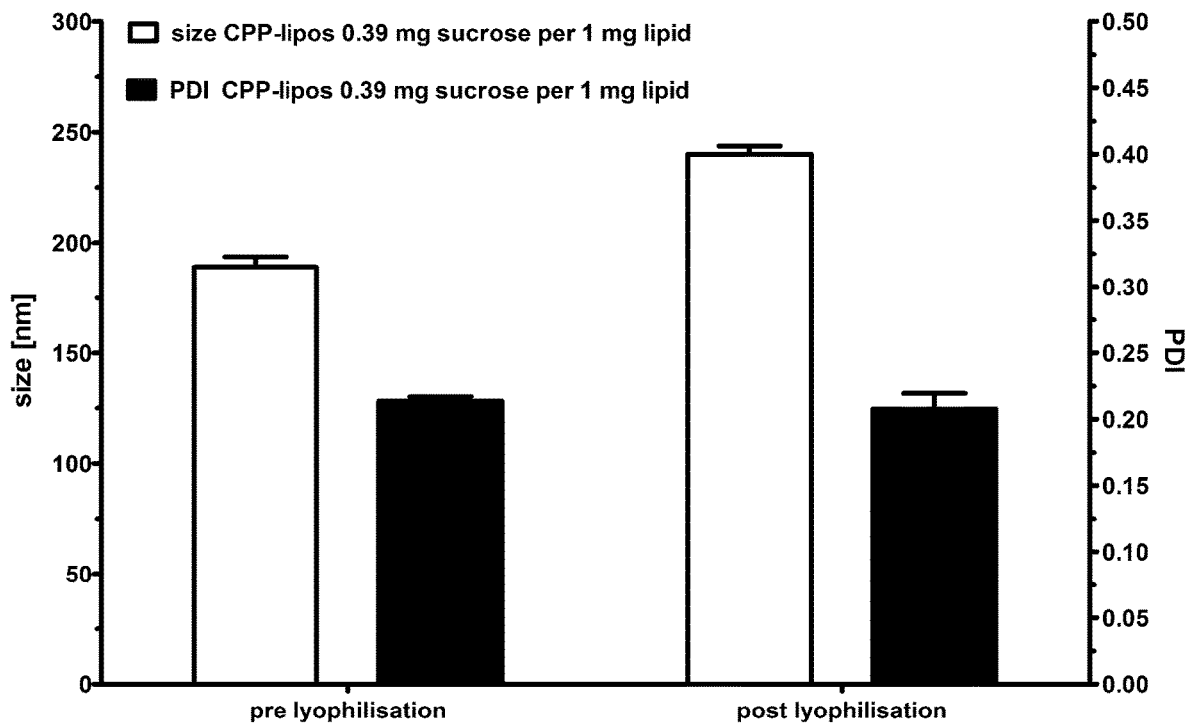
FIG. 6 Comparison of liposomal characteristics (size; PDI) before and after the lyophilisation process using different amounts of sucrose as lyoprotector.

Size and PDI Pre- and Post Lyophilisation (FIG. 6)

Comparison of the size and PDI of CPP-liposomes freeze dried with 0.39 mg sucrose per 1 mg lipid as lyoprotector. The successful lyophilisation is demonstrated by the constant size and PDI before and after the freeze-drying process.

Figure 7:
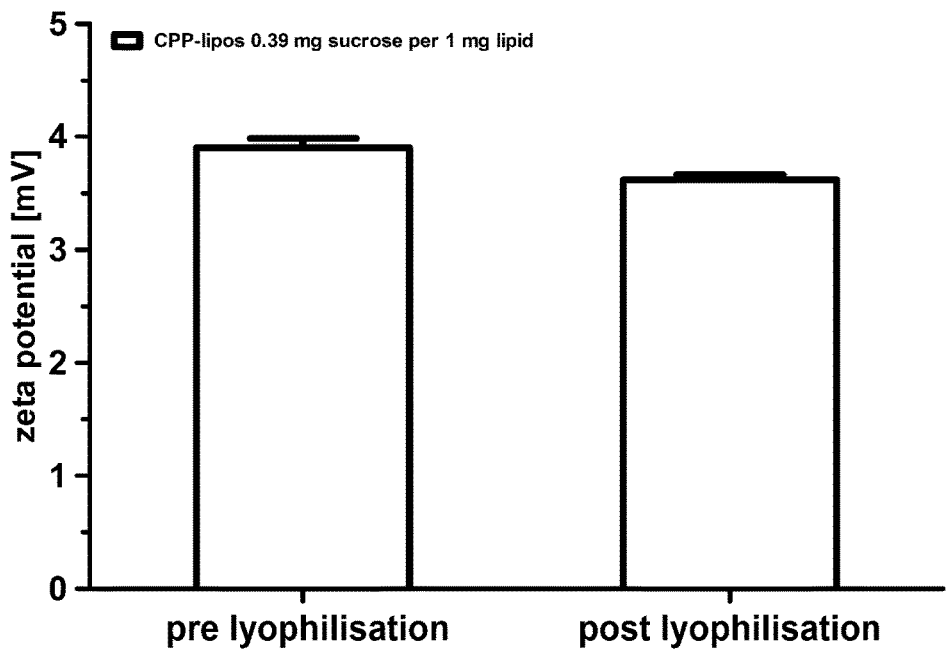
FIG. 7 Comparison of zeta potential of CPP-liposomes before and after the lyophilisation process.

Zeta Potential Pre- and Post Lyophilisation (FIG. 7)

Comparison of the zeta potential of CPP-liposomes freeze dried with 0.39 mg sucrose per 1 mg of lipid as lyoprotector. The successful lyophilisation is demonstrated by the constant zeta potential before and after the freeze-drying.

Figure 8:
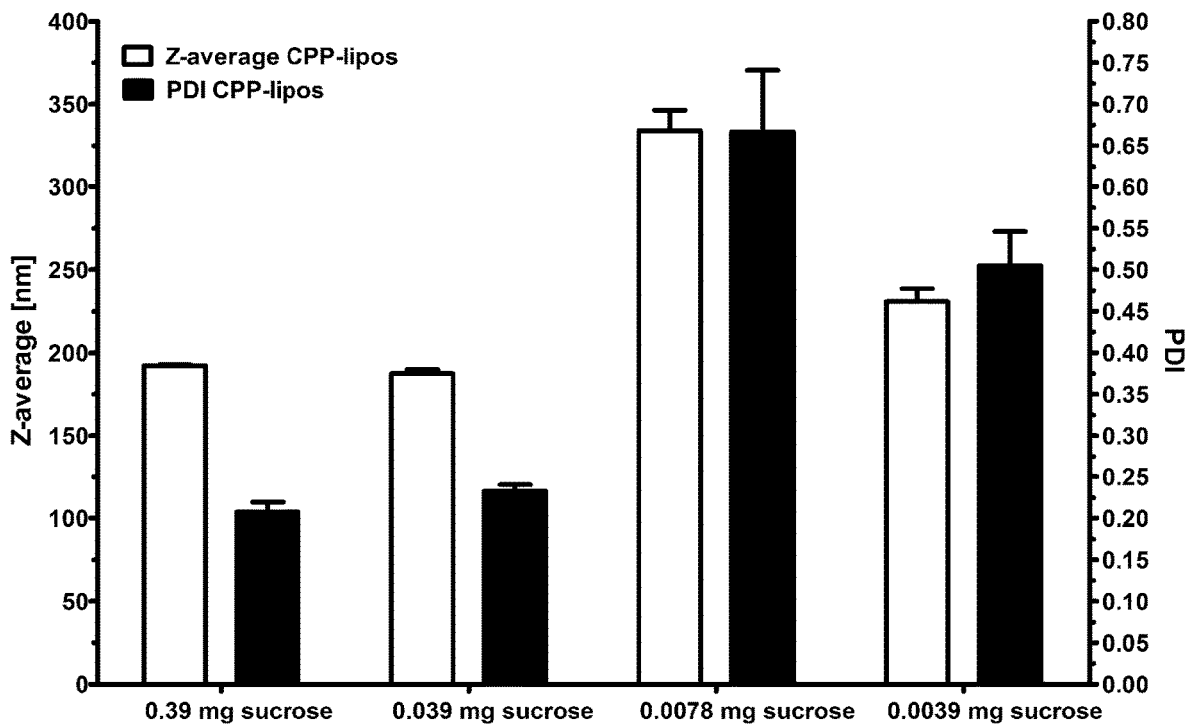
FIG. 8 Z-average and PDI of CPP-liposomes after lyophilisation with different amounts of sucrose as lyoprotector.

Z-Average and PDI of CPP-Liposomes Freeze Dried with Various Amounts of Sucrose as Lyoprotector (FIG. 8)

Comparison of the Z-average and PDI of CPP-liposomes freeze dried with various amounts of sucrose as lyoprotector (0.0039 mg-0.39 mg sucrose per 1 mg of lipid). The limit of lyophilisation is demonstrated by the strong increase in liposomal Z-average and PDI for the formulations freeze-dried with too low amounts of sucrose (0.0078 and 0.0039 mg of sucrose per 1 mg of lipid).

Figure 9:
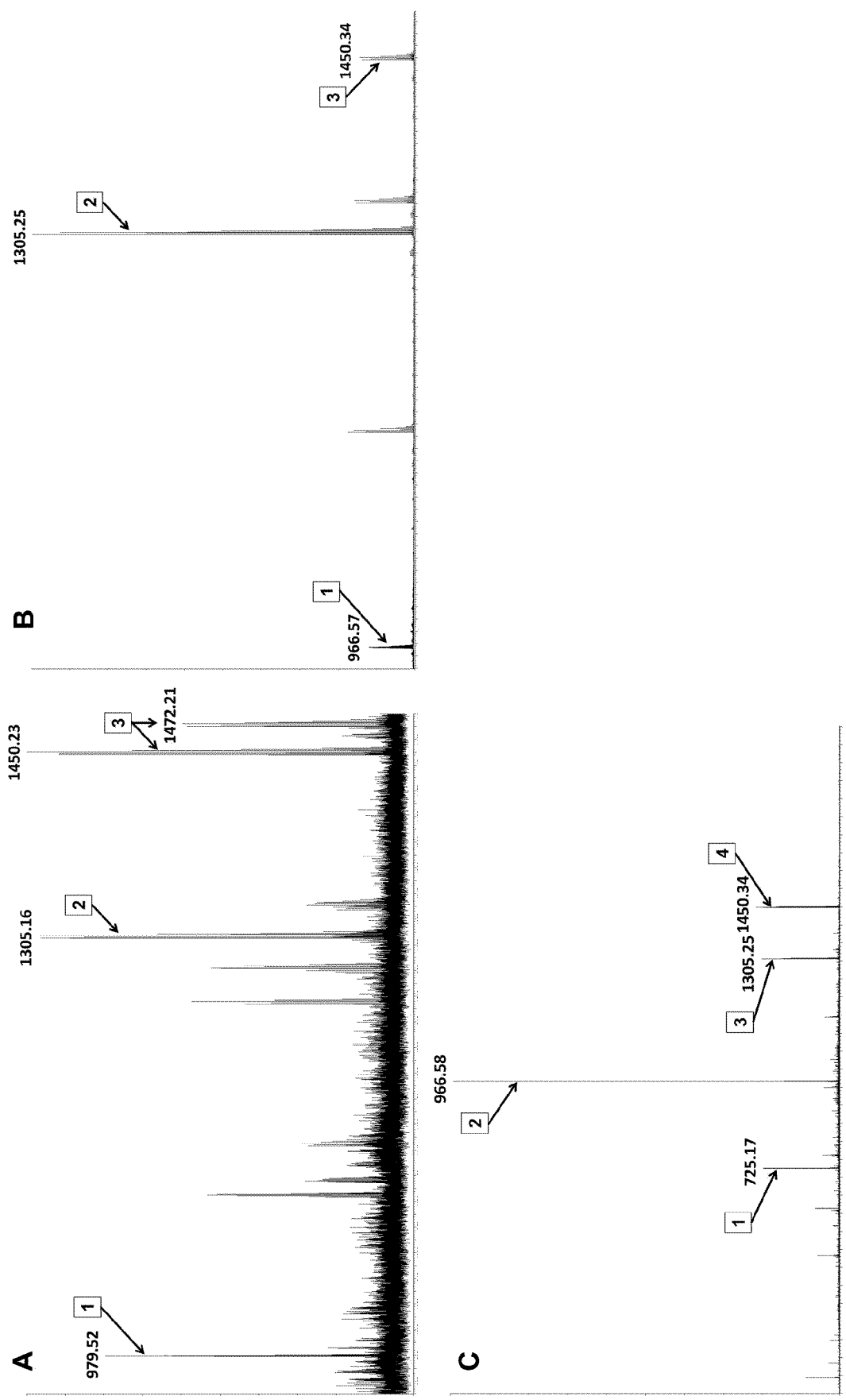
FIG. 9 Identification of modified API (vancomycin) after preparation of liposomes with activated first lipids for retrospective coupling of CPP.

Identification of Modified API (Vancomycin) after Preparation of Liposomes with Activated First Lipids (FIG. 9)

Comparison of the mass spectra of the API (vancomycin) after preparation of API containing CPP-liposomes and after preparation of API containing liposomes comprising activated first lipid (PEG(13)-distearoylphosphatidylethanolamine-tetrafluorophenyl ester) for retrospective coupling of CPP.

Liposomes were dissolved with MeOH/ACN/water 3/1/1+0.1% formic acid. High-resolution mass-spectra were recorded by direct infusion onto a Waters Xevo G2-XS QTof mass spectrometer.

A) Mass-spectrum of API containing CPP-liposomes. The numbered peaks correspond to: 1: $[M+3H]^{3+}$ peak of the CPP-lipid-conjugate of Tfp-PEG$_{13}$-DSPE and R9K-peptide, which was synthesized and purified prior to liposome preparation; 2: $[M+H]^+$ peak of desvancosamin-vancomycin, a fragment of vancomycin occurring in ionization of vancomycin; 3: $[M+H]^+$ and $[M+Na]^+$ peaks of vancomycin.

B) Mass-spectrum of API containing liposomes comprising activated first lipid for retrospective coupling of CPP. The numbered peaks correspond to: 1: peak corresponding to the conjugate of Tfp-PEG$_{13}$-DSPE and vancomycin, bearing a charge of 3. This was confirmed by the fragmentation of this signal at m/z 966.57 which yielded mainly daughter signals corresponding to vancomycin (FIG. 9 D); 2: $[M+H]^+$ peak of desvancosaminvancomycin, a fragment of vancomycin occurring in the ionization of vancomycin; 3: $[M+H]^+$ peak of vancomycin.

C) Mass-spectrum (daughter-spectrum) after collision-induced decomposition (CID) of the signal at m/z 966.57, which corresponds to the conjugate of Tfp-PEG$_{13}$-DSPE and vancomycin. Besides the parent peak (numbered as 2) of the non-fragmented conjugate of PEG(13)-distearoylphos-phatidylethanolamine-tetrafluorophenyl ester and vancomycin, CID-fragments are mainly signals corresponding to vancomycin: 1: $[M+2H]^{2+}$ peak of vancomycin; 3: $[M+H]^+$ peak of desvancosamine-vancomycin; and 4: $[M+H]^+$ peak of vancomycin.

Figure 10:
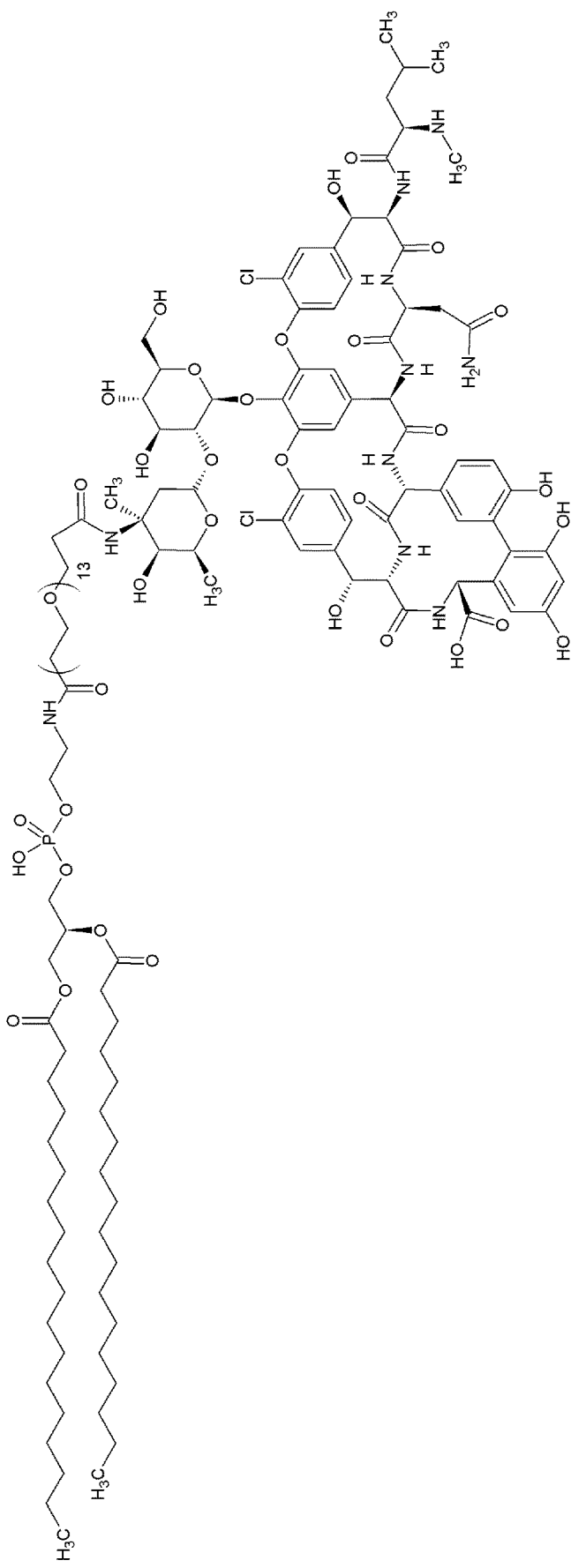
FIG. 10 Structure of the conjugate of API (vancomycin) and activated first lipid.

Structure of Modified API by Activated First Lipid (FIG. 10)

Structure of the conjugate of Tfp-PEG$_{13}$-DSPE and vancomycin identified after preparation of liposomes containing activated first lipid (detected by MS-analysis as described in FIG. 9). This figure shows the high benefit of the preparation method claimed in this invention, which can avoid such API-modifications by removing free, activated first lipid before the liposomal preparation.

Robustness of Liposomes to Changes in Buffer and API (FIG. 11 to 16)

The liposomes of this invention have great uniformity. This includes that important liposome properties remain unchanged, even if different buffers or active ingredients are used.

Figure 11:
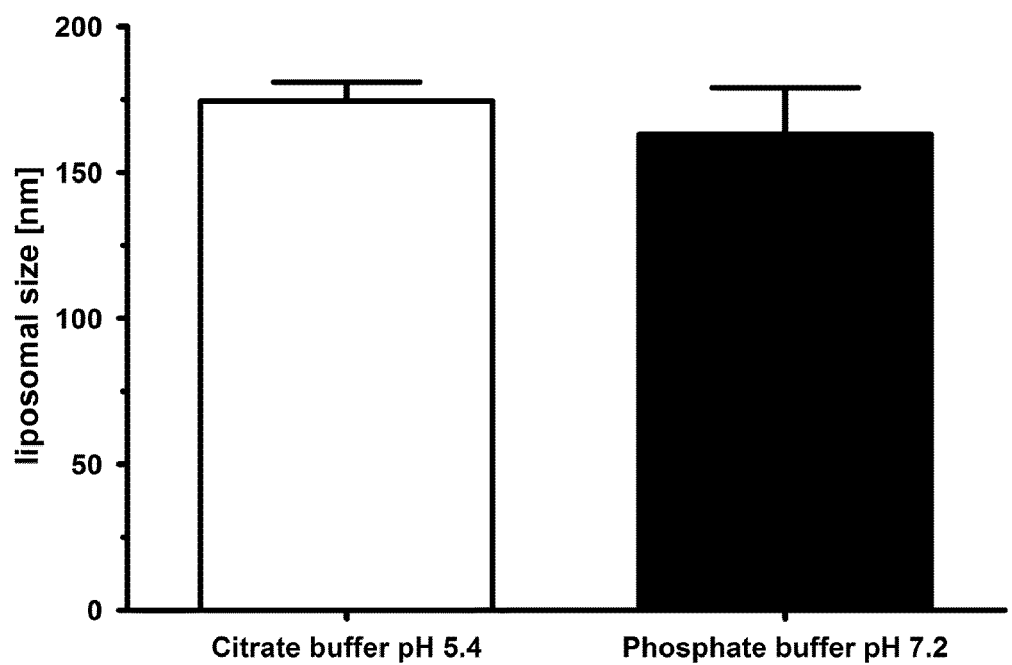
FIG. 11 Comparison of liposomal size in different buffers.
Figure 12:
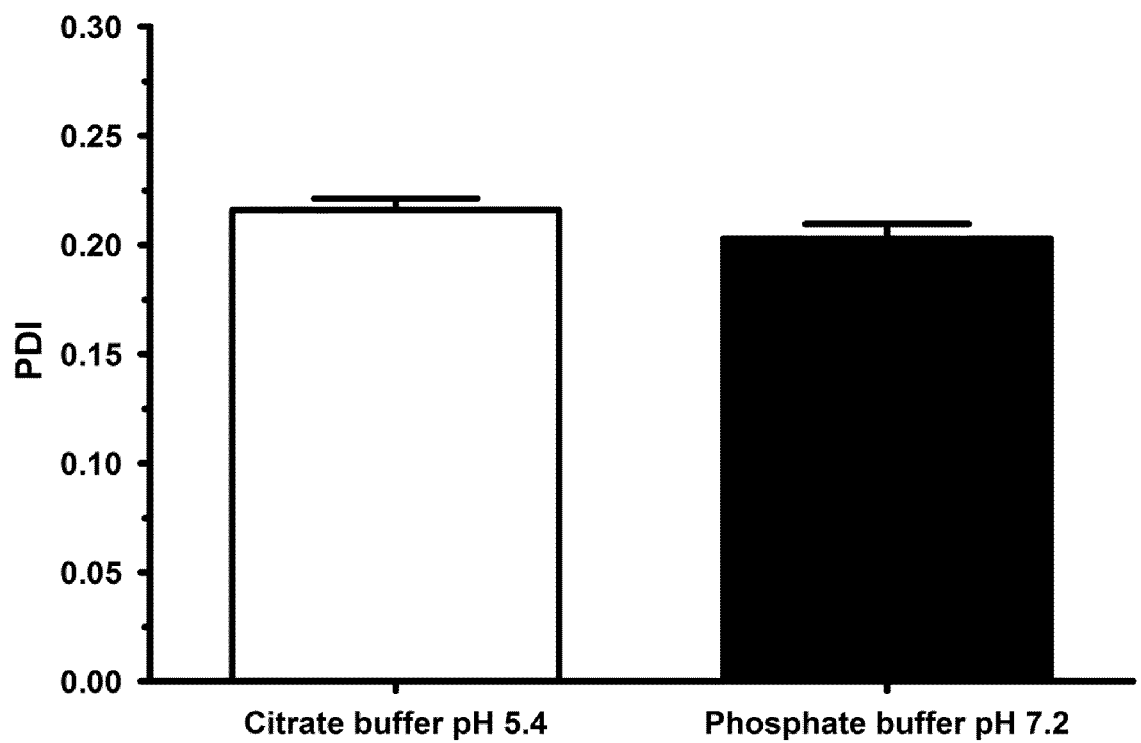
FIG. 12 Comparison of PCI in different buffers.
Figure 13:
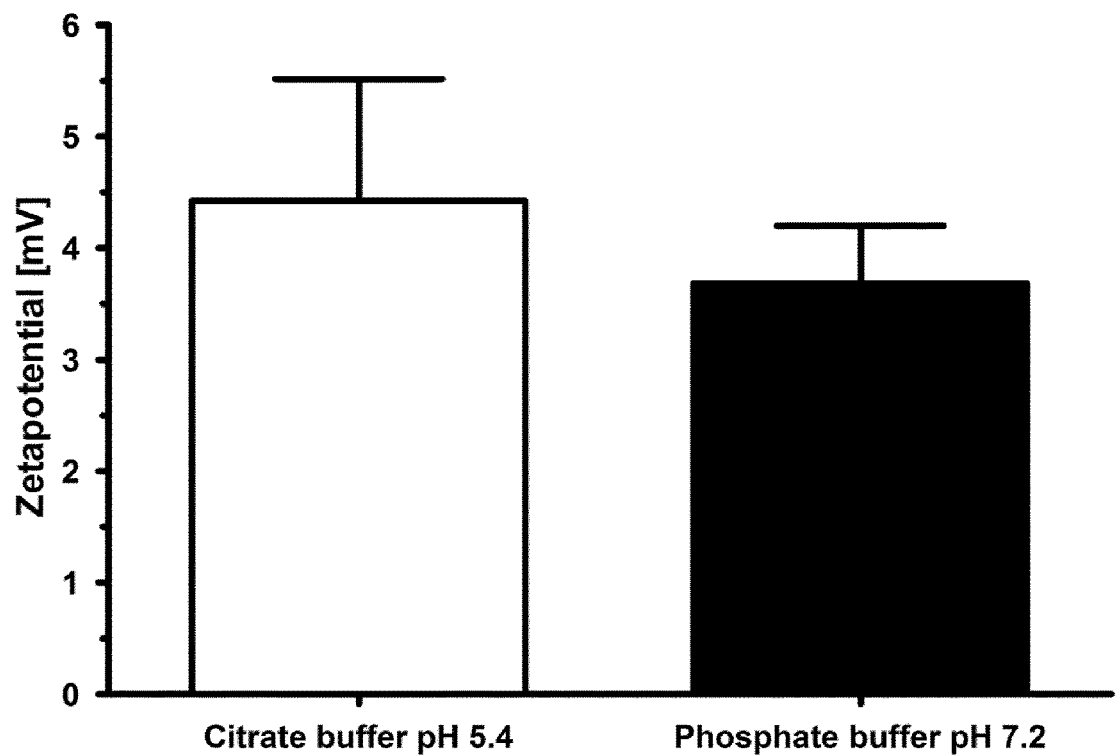
FIG. 13 Comparison of Zetapotential in different buffers.

Liposomes as prepared above were suspended in different buffers and their sizes, PDIs and Zetapotentials were measured. FIGS. 11, 12 and 13 confirm that these liposome parameters remain essentially unchanged despite a drastic change in pH from 5.4 to 7.2.

Figure 14:
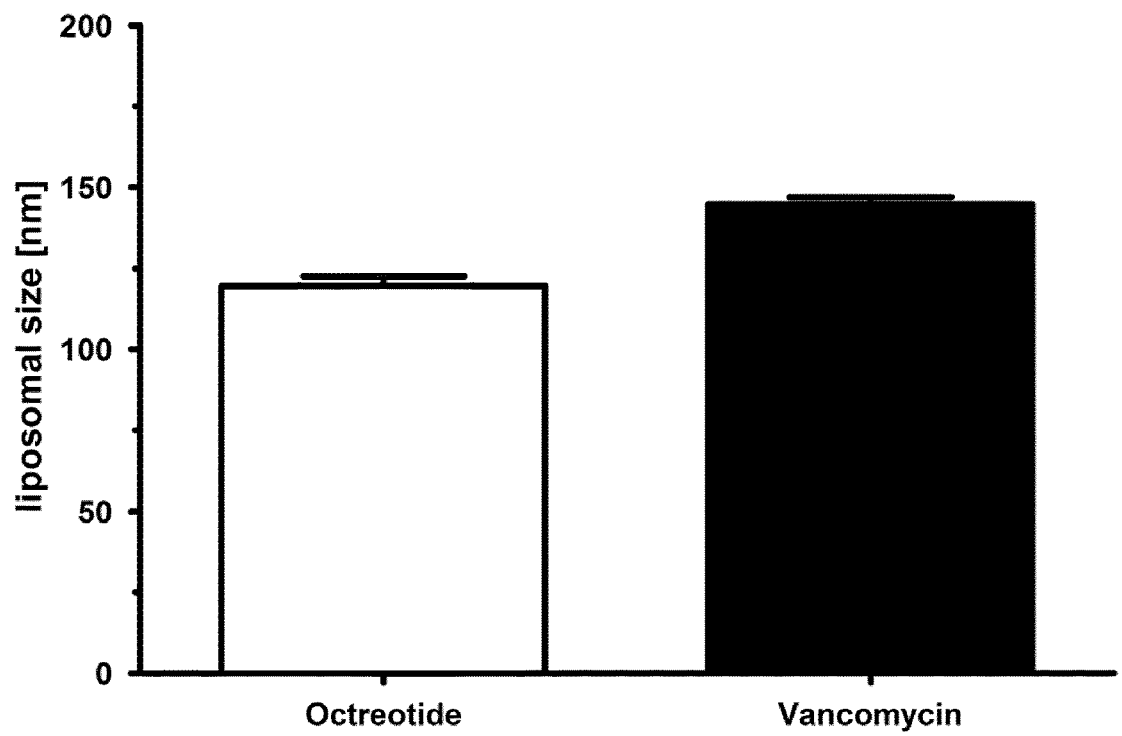
FIG. 14 Comparison of liposomal size with different APIs.
Figure 15:
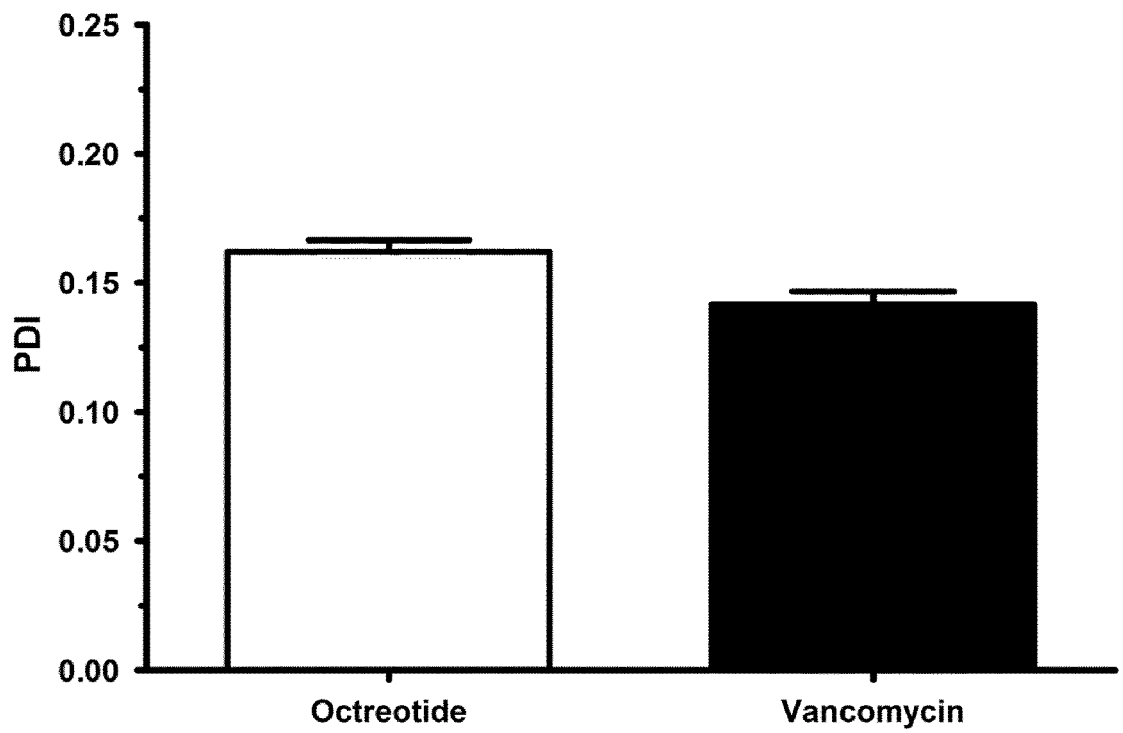
FIG. 15 Comparison of PCI with different APIs.
Figure 16:
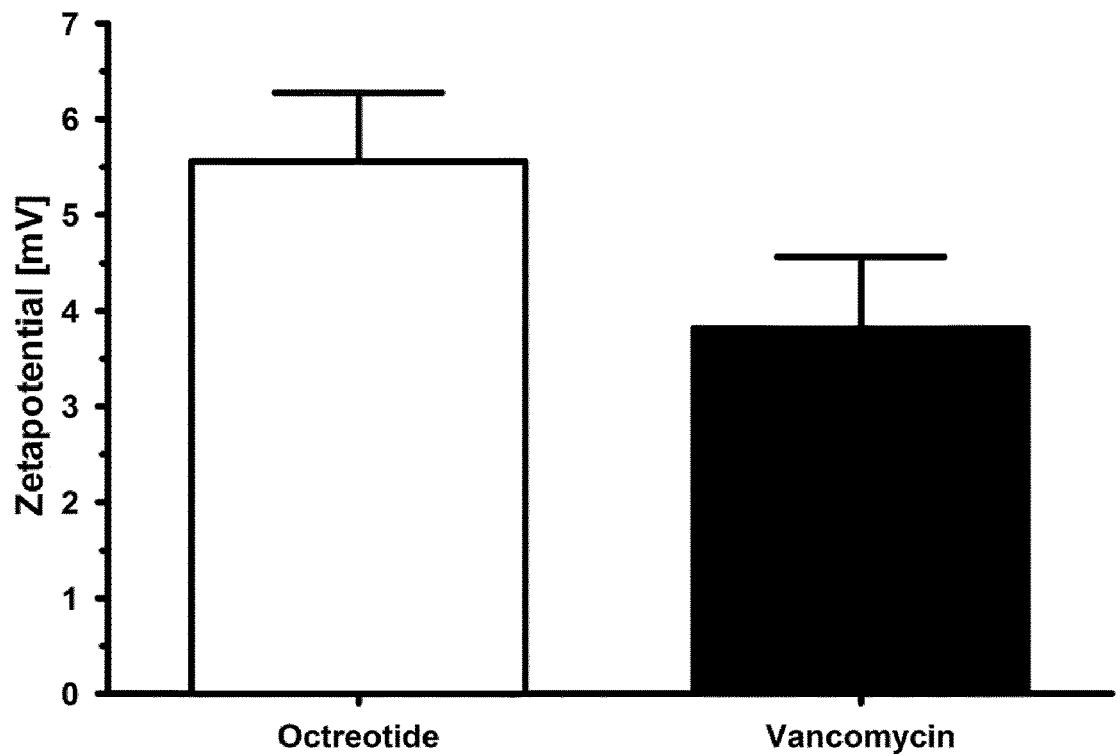
FIG. 16 Comparison of Zetapotential with different APIs.

In another experiment, liposomes were made using different active agents, namely octreotide and vancomycin. In both cases, 20 mg/ml of the API were used. FIGS. 14, 15 and 16 show that the important liposome parameters size, PDI and Zetapotential are hardly influenced.

The data confirm that the liposomes of this invention are very robust and allow for essentially constant liposome properties over a variety of different compositions and environments.

Mass Spectra of Insulin Containing Liposomes (FIGS. 17A to 18B)

Figure 17A:
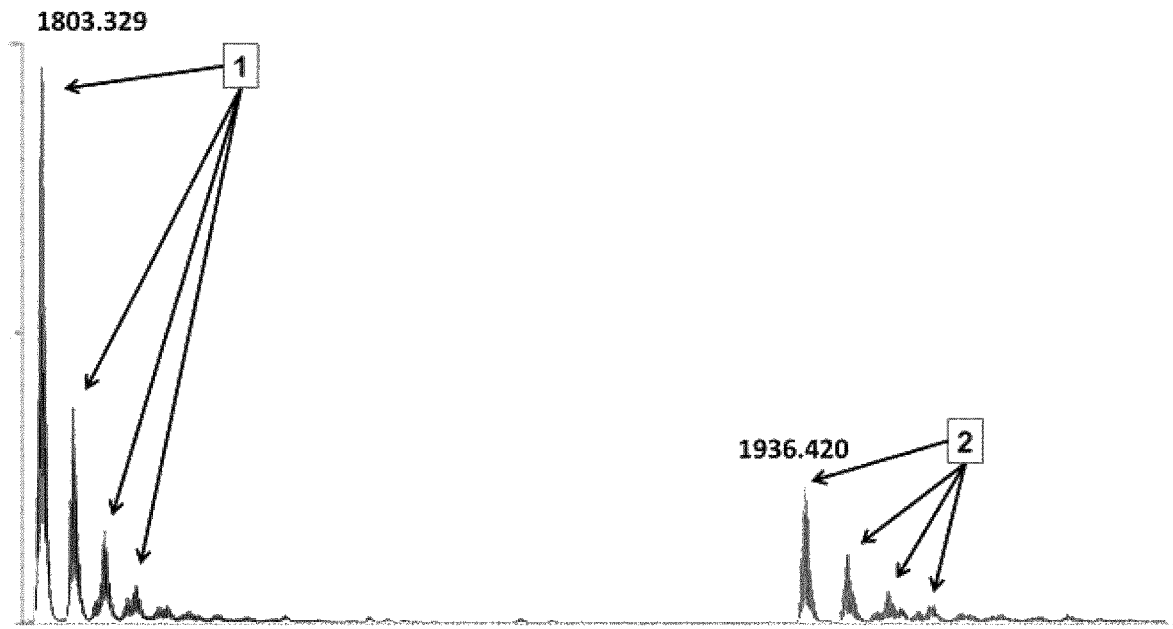
FIG. 17A High resolution mass spectrum of liposomal formulations of insulin comprising activated lipid Tfp-PEG$_{13}$-DSPE.

FIGS. 17A and B show high-resolution mass spectra of liposomal formulations of insulin comprising activated lipids during preparation for subsequent liposomal surface modification, acquired on a Waters Xevo GS-2-XS QTof.

Figure 18A:
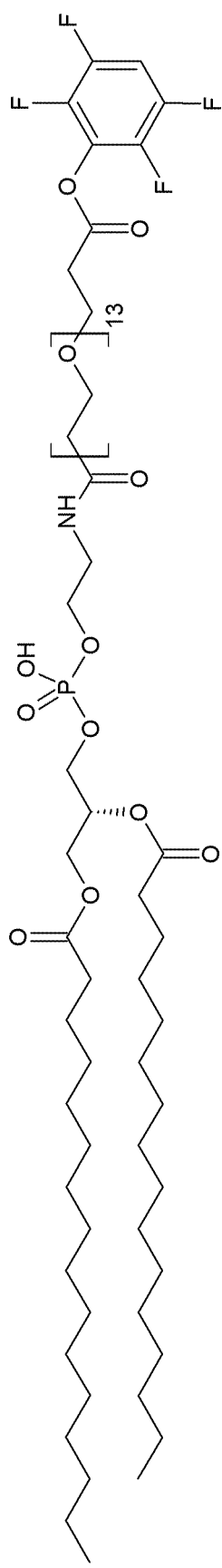
FIG. 18A Structure of Tfp-PEG$_{13}$-DSPE.

FIG. 17A relates to a liposomal formulation containing Tfp-PEG$_{13}$-DSPE. Visible is the z=3 peak of insulin and its sodium adducts at m/z 1936.420 and the z=4 signal of covalently modified insulin (by reaction with Tfp-PEG$_{13}$-DSPE) at m/z 1803.329 as well as the corresponding sodium adducts. FIG. 18A shows the structure of Tfp-PEG$_{13}$-DSPE. Tfp-PEG$_{13}$-DSPE can react with amino functions by substitution of the tetrafluorophenyl moiety.

Figure 17B:
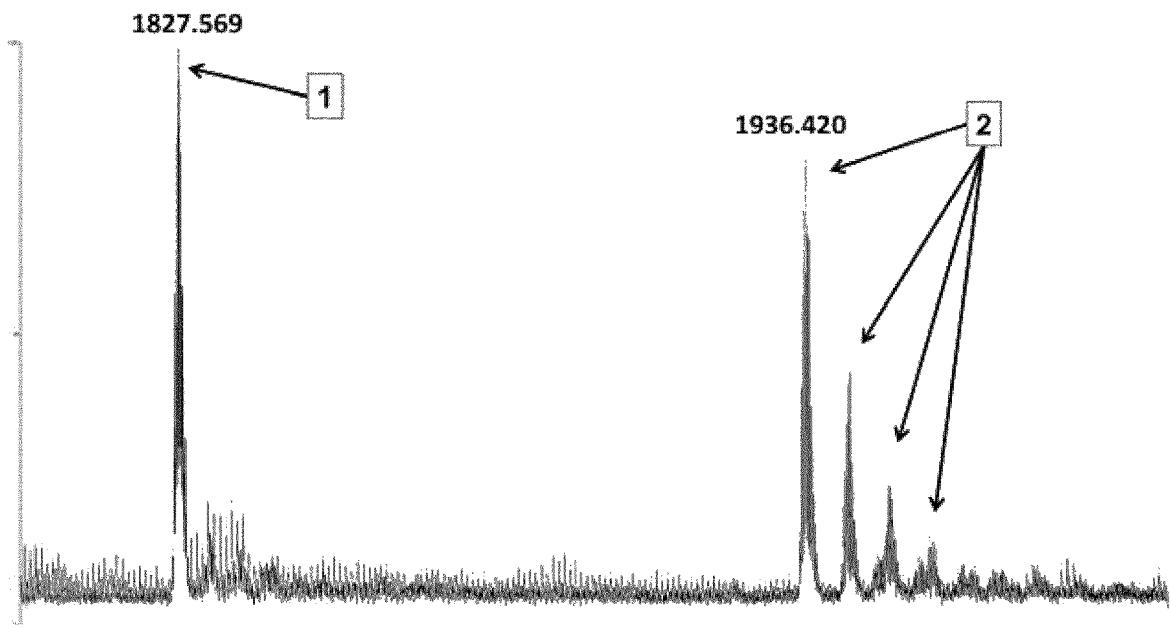
FIG. 17B High resolution mass spectrum of liposomal formulations of insulin comprising activated lipid Mal-PEG$_{12}$-DSPE.
Figure 18B:
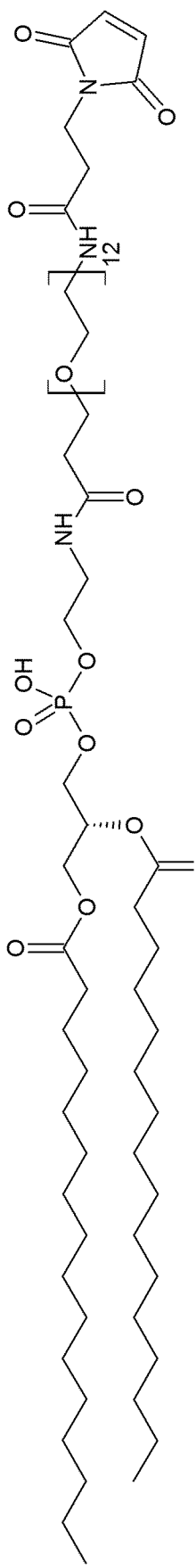
FIG. 18B Structure of Mal-PEG$_{12}$-DSPE.

FIG. 17B Liposomal formulation containing Mal-PEG$_{12}$-DSPE. Visible is the z=3 peak of insulin and its sodium adducts at m/z 1936.420 and the z=4 signal of covalently modified insulin (by reaction with Mal-PEG$_{12}$-DSPE) at m/z 1827.569. FIG. 18B shows the structure of Mal-PEG$_{12}$-DSPE. Mal-PEG$_{12}$-DSPE can react with thiol functions by Michael addition at the maleimide function.

FIGS. 17A and 17B show the high benefit of the preparation method of this invention, which can avoid API-modifications by removing free, activated first lipid before the liposomal preparation.

The invention claimed is:

1. A method of making an oral dosage form, comprising the steps of
   a. reacting at least one cell penetrating peptide (CPP) with at least one first lipid to obtain CPP-lipid conjugates, wherein the first lipid is 1,2-dioleoyl-sn-glycero-3-phosphoethanolamine-N-(succinyl) (sodium salt), and wherein the CPP-lipid conjugates have a molecular weight from 1,200 to 5,000 g/mol,
   b. purifying the CPP-lipid conjugates to obtain a purified CPP-lipid conjugate composition,
   c. preparing a lipid batch comprising at least
      c1. a defined amount of the CPP-lipid conjugates and
      c2. a defined amount of at least one non-CPP-conjugated second lipid, wherein the second lipid is different from the first lipid,
   d. processing the lipid batch to obtain CPP-modified liposomes having a zeta potential of more than 2 mV and less than 10 mV when measured in a solution of 50 mM phosphate buffer (pH 7.4) at a concentration of 0.95 mg/ml,
   e. lyophilizing the CPP-modified liposomes to obtain a liposome lyophilisate,
   f. incorporating the liposome lyophilisate into an oral dosage form,
   wherein the amount of non-conjugated first lipid in the purified CPP-lipid conjugate composition is less than 5 mol % relative to the total molar amount of CPP-lipid conjugates in said composition.

2. The method according to claim 1, wherein the CPP is selected from linear or cyclized polyargininines, linear or cyclized penetratin, linear or cyclized TAT (transactivator of transcription)-peptide, linear or cyclized MAP (model amphiphatic peptide), linear or cyclized pVEC, linear or cyclized transportan, and linear or cyclized MPG, dimers thereof, and combinations thereof.

3. The method according to claim 1, wherein the amount of CPP in the CPP-modified liposome is not more than 4 mol %, relative to the cumulative amount of first and second lipids in the liposome.

4. The method according to claim 1, wherein purifying the CPP-lipid conjugates to obtain a purified CPP-lipid conjugate composition includes the step of
   b1. separating CPP-lipid conjugates from non-conjugated first lipid, and
   b2. optionally separating CPP-lipid conjugates from non-conjugated CPP and/or conjugates carrying more than one CPP.

5. The method according to claim 1, wherein processing the lipid batch to obtain CPP-modified liposomes, includes high pressure homogenization, extrusion, ethanol injection and/or dual asymmetric centrifugation (DAC).

6. The method according to claim 1, wherein the CPP is a cyclic peptide.

7. The method according to claim 1, wherein the CPP-modified liposomes have a Z-average diameter in the range of from 50 nm to 250 nm.

8. The method according to claim 1, wherein the step of lyophilizing the CPP-modified liposomes to obtain a liposome lyophilisate includes:
   e1. preparing a mixture of the CPP-modified liposomes and at least one lyoprotector.

9. The method according to claim 8, wherein the lyoprotector is present in the mixture in a ratio of from 0.01 to 2 g of lyoprotector per 1 gram of lipid.

10. An oral dosage form comprising CPP-modified liposomes, having
- at least one CPP conjugated to a first lipid, wherein the first lipid is 1,2-dioleoyl-sn-glycero-3-phosphoethanolamine-N-(succinyl) (sodium salt), and wherein the CPP-lipid conjugates have a molecular weight from 1,200 to 5,000 g/mol;
- at least one non-CPP-conjugated second lipid, wherein the second lipid is different from the first lipid, and
- at least one pharmaceutically active ingredient, wherein the CPP-modified liposomes have a Z-average diameter in the range of from 50 nm to 250 nm, and a positive zeta potential in the range of from >2 mV to <10 mV when measured in a solution of 50 mM phosphate buffer (pH 7.4) at a concentration of 0.95 mg/ml.

11. The oral dosage form according to claim 10, obtainable by a method comprising the steps of
- a. reacting at least one CPP with at least one first lipid to obtain CPP-lipid conjugates,
- b. purifying the CPP-lipid conjugates to obtain a purified CPP-lipid conjugate composition,
- c. preparing a lipid batch comprising at least
  - c1. a defined amount of the CPP-lipid conjugates and
  - c2. a defined amount of at least one non-CPP-conjugated second lipid,
- d. processing the lipid batch to obtain CPP-modified liposomes having a zeta potential of more than 2 mV and less than 10 mV when measured in a solution of 50 mM phosphate buffer (pH 7.4) at a concentration of 0.95 mg/ml,
- e. lyophilizing the CPP-modified liposomes to obtain a liposome lyophilisate,
- f. incorporating the liposome lyophilisate into an oral dosage form, wherein the amount of non-conjugated first lipid in the purified CPP-lipid conjugate composition is less than 5 mol % relative to the total molar amount of CPP-lipid conjugates in said composition.

12. The oral dosage form according to claim 10, wherein the amount of non-conjugated first lipid in the CPP-modified liposomes is less than 5 mol %, relative to the total molar amount of CPP-lipid conjugates in the CPP-modified liposomes.

13. The oral dosage form according to claim 10, wherein the amount of CPP in the CPP-modified liposomes does not exceed 4 mol %, relative to the cumulative amount of first and second lipids in the liposome.

14. The oral dosage form according to claim 10, wherein
- the dosage form is selected from a tablet, a capsule, a pill, a powder, a liquid, a granulate, a pellet, a thin film, an effervescent formulation, a paste, a lozenge, a chewing gum, a gel, a spray or a combination thereof, and/or
- the oral dosage form is for use in a therapeutic method.

15. The method according to claim 1, wherein the CPP-lipid conjugates have a molecular weight of about 1,500 to about 3,500 g/mol.

16. The method according to claim 1, wherein CPP-lipid conjugates are separated from non-conjugated CPP and/or conjugates carrying more than one CPP in step b.

17. The method according to claim 1, wherein the amount of tetraether lipids in the liposomes is less than 0.01 mol %.

* * * * *